United States Patent
Dusankova et al.

(10) Patent No.: US 10,689,464 B2
(45) Date of Patent: Jun. 23, 2020

(54) SELF-SUPPORTING, BIODEGRADABLE FILM BASED ON HYDROPHOBIZED HYALURONIC ACID, METHOD OF PREPARATION AND USE THEREOF

(71) Applicant: Contipro a.s., Dolni Dobrouc (CZ)

(72) Inventors: Marcela Dusankova, Pardubice (CZ); Gloria Huerta-Angeles, Ceska Trebova (CZ); Kristina Nesporova, Usti Nad Orlici (CZ); Klara Slezingrova, Nekor (CZ); Antonin Minarik, Lipa (CZ); Josef Chmelar, Vsetin (CZ); Romana Sulakova, Usti nad Orlici (CZ); Sergej Karel, Usti nad Orlici (CZ); Vladimir Velebny, Zamberk (CZ)

(73) Assignee: Contipro a.s., Dolni Dobroue (CZ)

( * ) Notice: Subject to any disclaimer, the term of this patent is extended or adjusted under 35 U.S.C. 154(b) by 0 days.

(21) Appl. No.: 15/556,370

(22) PCT Filed: Mar. 9, 2016

(86) PCT No.: PCT/CZ2016/000027
§ 371 (c)(1),
(2) Date: Sep. 7, 2017

(87) PCT Pub. No.: WO2016/141903
PCT Pub. Date: Sep. 15, 2016

(65) Prior Publication Data
US 2018/0105610 A1    Apr. 19, 2018

(30) Foreign Application Priority Data

Mar. 9, 2015 (CZ) .............................. PV 2015-166

(51) Int. Cl.
| | | |
|---|---|---|
| *C08B 37/08* | (2006.01) | |
| *A61K 31/728* | (2006.01) | |
| *C08J 5/18* | (2006.01) | |
| *C08L 5/08* | (2006.01) | |
| *A61L 27/20* | (2006.01) | |
| *A61L 27/54* | (2006.01) | |
| *A61K 45/06* | (2006.01) | |
| *C08J 3/02* | (2006.01) | |
| *C08J 3/09* | (2006.01) | |
| *B29C 71/02* | (2006.01) | |

(52) U.S. Cl.
CPC ........ *C08B 37/0072* (2013.01); *A61K 31/728* (2013.01); *A61K 45/06* (2013.01); *A61L 27/20* (2013.01); *A61L 27/54* (2013.01); *C08J 3/02* (2013.01); *C08J 3/095* (2013.01); *C08J 5/18* (2013.01); *C08J 7/08* (2013.01); *C08L 5/08* (2013.01); *C08J 2305/08* (2013.01); *C08L 2201/06* (2013.01)

(58) Field of Classification Search
None
See application file for complete search history.

(56) References Cited

U.S. PATENT DOCUMENTS

| | | |
|---|---|---|
| 3,075,527 A | 1/1963 | Bechtold |
| 3,720,662 A | 3/1973 | Tessler et al. |
| 3,728,223 A | 4/1973 | Kaneko et al. |
| (Continued) | | |

FOREIGN PATENT DOCUMENTS

| | | |
|---|---|---|
| CA | 2512730 A1 | 7/2004 |
| CH | 628088 A5 | 2/1982 |
| (Continued) | | |

OTHER PUBLICATIONS

Foglarová, M., Chmelař, J., Huerta-Angeles, G., Vágnerová, H., Kulhánek, J., Tománková, K. B., . . . & Velebný, V. (2016). Water-insoluble thin films from palmitoyl hyaluronan with tunable properties. Carbohydrate polymers, 144, 68-75. (Year: 2016).*

Office Action in U.S. Appl. No. 14/113,527, dated Sep. 8, 2016, 10 pgs.

Office Action in U.S. Appl. No. 14/395,575, dated Jul. 6, 2017, 9 pgs.

Office Action in U.S. Appl. No. 14/420,012, dated Jun. 16, 2016, 6 pgs.

Office Action in U.S. Appl. No. 14/430,731, dated May 19, 2016, 12 pgs.

Office Action in U.S. Appl. No. 14/647,185, dated Sep. 28, 2016, 5 pgs.

(Continued)

*Primary Examiner* — Dale R Miller
(74) *Attorney, Agent, or Firm* — Wood Herron & Evans LLP

(57) ABSTRACT

The invention relates to a self-supporting, biodegradable film comprising a $C_{10}$-$C_{22}$-acylated derivative of hyaluronic acid according to the general formula (I), where R is $H^+$ or $Na^+$, and where $R^1$ is H or —C(=O)$C_xH_y$, where x is an integer within the range from 9 to 21 and y is an integer within the range from 11 to 43 and $C_xH_y$ is a linear or branched, saturated or unsaturated $C_9$-$C_{21}$ chain, wherein in at least one repeating unit one or more of $R^1$ is —C(=O)$C_xH_y$, and where n is within the range from 12 to 4000; a method of preparation thereof and use thereof.

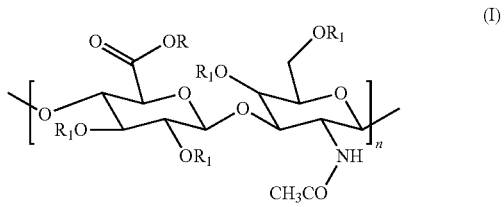

17 Claims, 5 Drawing Sheets

(56) References Cited

U.S. PATENT DOCUMENTS

| | | |
|---|---|---|
| 4,043,331 A | 8/1977 | Martin et al. |
| 4,205,025 A | 5/1980 | Hart et al. |
| 4,258,134 A | 3/1981 | Yoshida et al. |
| 4,713,448 A | 12/1987 | Balazs et al. |
| 4,761,401 A | 8/1988 | Couchman et al. |
| 4,851,521 A | 7/1989 | Della Valle et al. |
| 4,965,353 A | 10/1990 | Della Valle et al. |
| 5,455,349 A | 10/1995 | Grasshoff et al. |
| 5,462,976 A | 10/1995 | Matsuda et al. |
| 5,520,916 A | 5/1996 | Dorigatti et al. |
| 5,522,879 A | 6/1996 | Scopelianos |
| 5,550,225 A | 8/1996 | Philippe |
| 5,616,568 A | 4/1997 | Pouyani et al. |
| 5,658,582 A | 8/1997 | Dorigatti et al. |
| 5,676,964 A | 10/1997 | Della Valle et al. |
| 5,690,961 A | 11/1997 | Nguyen |
| 5,824,335 A | 10/1998 | Dorigatti et al. |
| 5,868,973 A | 2/1999 | Muller et al. |
| 6,025,444 A | 2/2000 | Waki et al. |
| 6,075,066 A | 6/2000 | Matsuda et al. |
| 6,162,537 A | 12/2000 | Martin et al. |
| 6,207,134 B1 | 3/2001 | Fahlvik et al. |
| 6,288,043 B1 | 9/2001 | Spiro et al. |
| 6,509,039 B1 | 1/2003 | Nies |
| 6,613,897 B1 | 9/2003 | Yatsuka et al. |
| 6,632,802 B2 | 10/2003 | Bellini et al. |
| 6,641,798 B2 | 11/2003 | Achilefu et al. |
| 6,673,919 B2 | 1/2004 | Yui et al. |
| 6,683,064 B2 | 1/2004 | Thompson et al. |
| 6,719,986 B1 | 4/2004 | Wohlrab et al. |
| 6,902,548 B1 | 6/2005 | Schuler et al. |
| 6,953,784 B2 | 10/2005 | Thompson et al. |
| 7,125,860 B1 | 10/2006 | Renier et al. |
| 7,214,759 B2 | 5/2007 | Pacetti et al. |
| 7,345,117 B1 | 3/2008 | Barbucci et al. |
| 7,550,136 B2 | 6/2009 | Warner et al. |
| 7,680,038 B1 | 3/2010 | Gourlay |
| 7,951,936 B2 | 5/2011 | Sato |
| 8,062,654 B2 | 11/2011 | Nelson et al. |
| 8,129,449 B2 | 3/2012 | Heinzman et al. |
| 8,143,391 B2 | 3/2012 | Yasugi et al. |
| 8,247,546 B2 | 8/2012 | Stucchi et al. |
| 9,017,725 B2 | 4/2015 | Mitra et al. |
| 9,492,586 B2 | 11/2016 | Wolfova et al. |
| 9,522,966 B2 | 12/2016 | Buffa et al. |
| 2002/0016472 A1 | 2/2002 | Tsien et al. |
| 2002/0026039 A1 | 2/2002 | Bellini et al. |
| 2002/0076810 A1 | 6/2002 | Radice et al. |
| 2003/0113354 A1 | 6/2003 | Schmid et al. |
| 2003/0163073 A1 | 8/2003 | Effing et al. |
| 2003/0205839 A1 | 11/2003 | Bachrach |
| 2004/0101546 A1 | 5/2004 | Gorman et al. |
| 2004/0192643 A1 | 9/2004 | Pressato et al. |
| 2005/0112349 A1 | 5/2005 | Laurencin et al. |
| 2005/0118231 A1 | 6/2005 | El Meski et al. |
| 2005/0119219 A1 | 6/2005 | Bellini et al. |
| 2005/0126338 A1 | 6/2005 | Yadav |
| 2005/0266546 A1 | 12/2005 | Warner et al. |
| 2006/0046590 A1 | 3/2006 | Chu et al. |
| 2006/0084759 A1 | 4/2006 | Calabro et al. |
| 2006/0188578 A1 | 8/2006 | Fernandez et al. |
| 2006/0189516 A1 | 8/2006 | Yang et al. |
| 2006/0216324 A1 | 9/2006 | Stucke et al. |
| 2006/0281912 A1 | 12/2006 | James et al. |
| 2007/0149441 A1 | 6/2007 | Aeschlimann et al. |
| 2007/0202084 A1 | 8/2007 | Sadozai et al. |
| 2008/0009630 A1 | 1/2008 | Gao et al. |
| 2008/0063617 A1 | 3/2008 | Abrahams et al. |
| 2008/0071001 A1 | 3/2008 | Sato |
| 2008/0124395 A1 | 5/2008 | Chen et al. |
| 2008/0286300 A1 | 11/2008 | Bardotti et al. |
| 2009/0024019 A1 | 1/2009 | Stein et al. |
| 2009/0028788 A1 | 1/2009 | Achilefu |
| 2009/0180966 A1 | 7/2009 | Borbely et al. |
| 2009/0252810 A1 | 10/2009 | Tommeraas et al. |
| 2010/0002155 A1 | 1/2010 | Yamaguchi et al. |
| 2010/0172892 A1 | 7/2010 | Uvarkina et al. |
| 2010/0207078 A1 | 8/2010 | Marder et al. |
| 2010/0247908 A1 | 9/2010 | Velev et al. |
| 2010/0310631 A1 | 12/2010 | Domard et al. |
| 2010/0310853 A1 | 12/2010 | Schwiegk et al. |
| 2010/0316682 A1 | 12/2010 | Chen et al. |
| 2011/0020917 A1 | 1/2011 | Wen et al. |
| 2011/0028062 A1 | 2/2011 | Chester et al. |
| 2011/0104070 A1 | 5/2011 | Kang et al. |
| 2011/0111012 A1 | 5/2011 | Pepper et al. |
| 2011/0196328 A1 | 8/2011 | Bellini et al. |
| 2011/0200676 A1 | 8/2011 | Lin et al. |
| 2011/0218331 A1 | 9/2011 | Buffa et al. |
| 2011/0229551 A1 | 9/2011 | Doshi et al. |
| 2011/0263724 A1 | 10/2011 | Gurtner et al. |
| 2012/0040463 A1 | 2/2012 | Domard et al. |
| 2012/0095205 A1 | 4/2012 | Buffa et al. |
| 2012/0245323 A1 | 9/2012 | Buffa et al. |
| 2012/0264913 A1 | 10/2012 | Buffa et al. |
| 2012/0277416 A1 | 11/2012 | Carter et al. |
| 2012/0289478 A1 | 11/2012 | Rovati |
| 2013/0017367 A1* | 1/2013 | Ravagnan ............... C23C 14/22 428/144 |
| 2013/0136784 A1 | 5/2013 | Staab |
| 2013/0195791 A1 | 8/2013 | Berkland et al. |
| 2013/0309706 A1 | 11/2013 | Kruglick |
| 2014/0120069 A1 | 5/2014 | Huerta-Angeles et al. |
| 2014/0242145 A1 | 8/2014 | Yoo et al. |
| 2015/0157463 A1 | 6/2015 | Stad et al. |
| 2015/0320873 A1 | 11/2015 | Smejkalova et al. |

FOREIGN PATENT DOCUMENTS

| | | |
|---|---|---|
| CN | 101897976 A | 12/2010 |
| CN | 102154738 A | 8/2011 |
| CN | 103505736 A | 1/2014 |
| CN | 103789874 A | 5/2014 |
| CZ | 2006605 A3 | 4/2008 |
| CZ | 20070299 A3 | 2/2009 |
| CZ | 301899 B6 | 7/2010 |
| CZ | 302503 B6 | 6/2011 |
| CZ | 302504 B6 | 6/2011 |
| CZ | 302856 B6 | 12/2011 |
| CZ | 302994 B6 | 2/2012 |
| CZ | 20101001 A3 | 2/2012 |
| CZ | 303879 B6 | 6/2013 |
| CZ | 304072 B6 | 9/2013 |
| CZ | 304266 B6 | 2/2014 |
| CZ | 304303 B6 | 2/2014 |
| CZ | 20120537 A3 | 3/2014 |
| CZ | 304512 B6 | 6/2014 |
| CZ | 305153 B6 | 5/2015 |
| DE | 10331342 A1 | 2/2005 |
| EP | 0161887 A2 | 11/1985 |
| EP | 0216453 A2 | 4/1987 |
| EP | 0763754 A2 | 3/1997 |
| EP | 0554898 B1 | 5/1997 |
| EP | 1369441 A1 | 12/2003 |
| EP | 1454913 A1 | 9/2004 |
| EP | 1115433 B1 | 12/2004 |
| EP | 1538166 A1 | 6/2005 |
| EP | 1217008 B1 | 3/2006 |
| EP | 1826274 A1 | 8/2007 |
| EP | 1905456 A1 | 4/2008 |
| EP | 1607405 B1 | 5/2011 |
| EP | 2399940 A2 | 12/2011 |
| EP | 2522337 A2 | 11/2012 |
| EP | 2899214 A1 | 7/2015 |
| JP | 62104579 A | 5/1987 |
| JP | 63044883 A | 11/1988 |
| JP | H0214019 A | 1/1990 |
| JP | H0347801 A | 2/1991 |
| JP | 06025306 A | 2/1994 |
| JP | H0625306 A | 2/1994 |
| JP | 3308742 B2 | 7/2002 |
| JP | 2004507586 A | 3/2004 |
| JP | 2004123785 A | 4/2004 |
| JP | 2007262595 A | 10/2007 |

(56) References Cited

FOREIGN PATENT DOCUMENTS

| | | |
|---|---|---|
| JP | 3975267 B2 | 12/2007 |
| JP | 2008208480 A | 9/2008 |
| JP | 2008295885 A | 12/2008 |
| JP | 2010138276 A | 6/2010 |
| KR | 20070118730 A | 12/2007 |
| KR | 20080062092 A | 7/2008 |
| KR | 20080111815 A | 12/2008 |
| KR | 20120118681 A | 10/2012 |
| KR | 20130085294 A | 7/2013 |
| NL | 9700003 A | 7/1997 |
| WO | 199311803 A1 | 6/1993 |
| WO | 199627615 A1 | 9/1996 |
| WO | 9635720 A1 | 11/1996 |
| WO | 9637519 A1 | 11/1996 |
| WO | 199808876 A1 | 3/1998 |
| WO | 199901143 A1 | 1/1999 |
| WO | 199957158 A1 | 11/1999 |
| WO | 0063470 A1 | 10/2000 |
| WO | 0134657 A1 | 5/2001 |
| WO | 0218448 A2 | 3/2002 |
| WO | 0218450 A1 | 3/2002 |
| WO | 0232913 A1 | 4/2002 |
| WO | 2002032285 A2 | 4/2002 |
| WO | 0248197 A1 | 6/2002 |
| WO | 02057210 A1 | 7/2002 |
| WO | 2004061171 A2 | 7/2004 |
| WO | 2005028632 A2 | 3/2005 |
| WO | 2005092390 A2 | 10/2005 |
| WO | 2005092929 A1 | 10/2005 |
| WO | 2006010066 A2 | 1/2006 |
| WO | 2006026104 A2 | 3/2006 |
| WO | 2006056204 A1 | 6/2006 |
| WO | 2006102374 A2 | 9/2006 |
| WO | 2007003905 A1 | 1/2007 |
| WO | 2007006403 A2 | 1/2007 |
| WO | 2007009728 A2 | 1/2007 |
| WO | 2007033677 A1 | 3/2007 |
| WO | 2007101243 A1 | 9/2007 |
| WO | 2008014787 A1 | 2/2008 |
| WO | 2008031525 A1 | 3/2008 |
| WO | 2008077172 A2 | 7/2008 |
| WO | 2008115799 A1 | 9/2008 |
| WO | 2009037566 A2 | 3/2009 |
| WO | 2009050389 A2 | 4/2009 |
| WO | 2009108100 A1 | 9/2009 |
| WO | 2009148405 A1 | 12/2009 |
| WO | 2010018324 A1 | 2/2010 |
| WO | 2010028025 A1 | 3/2010 |
| WO | 2010051783 A1 | 5/2010 |
| WO | 2010061005 A1 | 6/2010 |
| WO | 2010095049 A1 | 8/2010 |
| WO | 2010095052 A2 | 8/2010 |
| WO | 2010095056 A2 | 8/2010 |
| WO | 2010105582 A1 | 9/2010 |
| WO | 2010130810 A1 | 11/2010 |
| WO | 2010138074 A1 | 12/2010 |
| WO | 2011014432 A1 | 2/2011 |
| WO | 2011028031 A2 | 3/2011 |
| WO | 2011059325 A2 | 5/2011 |
| WO | 2011059326 A2 | 5/2011 |
| WO | 2011069474 A2 | 6/2011 |
| WO | 2011069475 A2 | 6/2011 |
| WO | 2012034544 A2 | 3/2012 |
| WO | 2012089179 A1 | 7/2012 |
| WO | 2012146218 A1 | 11/2012 |
| WO | 2013056312 A1 | 4/2013 |
| WO | 2013159757 A1 | 10/2013 |
| WO | 2013167098 A2 | 11/2013 |
| WO | 2013171764 A2 | 11/2013 |
| WO | 2014023272 A1 | 2/2014 |
| WO | 2014082608 A1 | 6/2014 |
| WO | 2014082609 A1 | 6/2014 |
| WO | 2014082611 A1 | 6/2014 |

OTHER PUBLICATIONS

Office Action in U.S. Appl. No. 14/647,626, dated Feb. 17, 2017, 12 pgs.
Office Action in U.S. Appl. No. 14/647,626, dated Jul. 28, 2016, 35 pgs.
Office Action in U.S. Appl. No. 14/647,626, dated Jun. 16, 2017, 14 pgs.
Office Action in U.S. Appl. No. 14/647,649, dated May 31, 2017, 11 pgs.
Office Action in U.S. Appl. No. 15/322,776, dated Jul. 14, 2017, 11 pgs.
Office Action in U.S. Appl. No. 15/322,776, dated Sep. 12, 2017, 23 pgs.
Oh, E.J. et al., "Target specific and long-acting delivery of protein, peptide, and nukleotide therapeutics using hyaluronic acid derivatives," J. Controlled Release vol. 141, 2010, pp. 2-12.
Pal, K. et al., "Biopolymers in Controlled-Release Delivery Systems," Modem Biopolymer Science (2009) 519-557.
Park, Y.D. et al., "Photopolymerized hyaluronic acid-based hydrogels and interpenetrating networks," Biomaterials (2003) 24:893-900.
Patel, P.K. et al., "Kinetic studies on the oxidation of phenols by the horseradish peroxidase compound II," Biochim Biophys Acta (1997) 1339(1):79-87.
Piluso, S. et al., "Hyaluronic acid-based hydrogels crosslinked by copper-catalyzed azide-alkyne cycloaddition with tailorable mechanical properties," International Journal of Artificial Organs (2011) 34:192-197, Abstract.
Prestwich, G.D., "Biomaterials from Chemically-Modified Hyaluronan," internet article, Feb. 26, 2001, 17 pgs.
Prestwich, G.D., "Hyaluronic acid-based clinical biomaterials derived for cell and molecule delivery in regenerative medicine," Journal of Controlled Release (2011) 155:193-199.
Qiu, Y. et al., "Environment-sensitive hydrogels for drug delivery," Advanced Drug Delivery Reviews (2001) 53:321-339.
Rao, K.V.R. et al., "Influence of Molecular Size and Water Solubility of the Solute on its Release from Swelling and Erosion Controlled Polymeric Matrices," Journal of Controlled Release (1990) 12:133-141.
Remy, H., Anorganicka chemie II., Sntl Praha 1971, pp. 306-321.
Ritger, P.L. et al., "A Simple Equation for Description of Solute Release I. Fickian and Non-Fickian Release from Non-Swellable Devices in the Form of Slabs, Spheres, Cylinders or Discs," Journal of Controlled Release (1987) 5:23-36.
Ritger, P.L. et al., "A Simple Equation for Description of Solute Release II. Fickian and Anomalous Release from Swellable Devices," Journal of Controlled Release (1987) 5:37-42.
Rostovtsev, V.V. et al., "A Stepwise Huisgen Cycloaddition Process: Copper(I)-Catalyzed Regioselective 'Ligation' of Azides and Terminal Alkynes," Angew. Chem. Int. Ed. (2002) 41(14):2596-2599.
Ruoslahti, E. et al., "Targeting of drugs and nanoparticles to tumors," The Journal of Cell Biology (2010) 188(6):759-768.
Rupprecht, A., Wet Spinning of Hyaluronic Acid. Preparation of Oriented Samples; Acta Chemica Scandinavica; 1979; 33; 779-780.
Sahiner, N. et al., "Fabrication and characterization of cross-linkable hydrogel particles based on hyaluronic acid: potential application in volcal fold regeneration", Journal of Biomaterials Science, Polymer Edition, vol. 19, Issue 2, pp. 223-243.
Schante, C.E. et al., "Chemical modifications of hyaluronic acid for the synthesis of derivatives for a broad range of biomedical applications," Carbohydrate Polymers (2011) 85:469-489.
Scott, J.E. et al., "Periodate Oxidation of Acid Polysaccharides", Histochemie, Apr. 26, 1969, vol. 19, pp. 155-161.
Scott, J.E. et al., "Secondary and tertiary structures of hyaluronan in aqueous solution, investigated by rotary shadowing—electron microscopy and computer simulation," J. Biochem vol. 274, 1991, pp. 699-705.
Sedova, P. et al., "Preparation of hyaluronan polyaldehyde—a precursor of biopolymer conjugates," Carbohydrate Research (2013) 371:8-15.
Seidlits, S.K. et al., "The effects of hyaluronic acid hydrogels with tunable mechanical properties on neural progenitor cell differentiation" Biomaterials (2010) 31:3930-3940.

(56) References Cited

OTHER PUBLICATIONS

Shang, J. et al., "Chitosan-based electroactive hydrogel," Polymer (2008) 49:5520-5525.

Sheehan, J.K. et al., "X-ray Diffraction Studies on the Connective Tissue Polysaccharides," J. Mol. Biol. (1975) 91:153-163.

Shen, Y. et al., "Synthesis and characterization of low molecular weight hyaluronic acid-based cationic micelles for efficient siRNA delivery," Carbohydrate Polymers (2009) 77(1):95-104.

Shen, Yi et al., "Synthesis, Characterization, Antibacterial and Antifungal Evaluation of Novel Monosaccharide Esters," Molecules (2012) 17(7):8661-8673.

Shimizu, M. et al., "Studies on hyaluronidase, chondroitin sulphatase, proteinase and phospholipase secreted by Candida species," Mycoses (1996) 39:161-167.

Shutava, T. et al., "Microcapsule Modification with Peroxidase-Catalyzed Phenol Polymerization," Biomacromolecules (2004) 5(3):914-921.

Sieburth, S.M. et al., "Fusicoccin Ring System by [4+4] Cycloaddition. 2. A Model Study," Tetrahedron Letters (1999) 40:4007-4010.

Sieburth, S.M. et al., "The [4+4] Cycloaddition and its Strategic Application in Natural Product Synthesis," Tetrahedron (1996) 52(18):6251-6282.

Slaughter, B.V. et al., "Hydrogels in Regenerative Medicine," Advanced Materials (2009) 21(32-33):3307-3329.

Slezingrova, K. et al., "Synteza a charakterizace palmitoyl hyaluronanu," Chemicke Listy (2012) 106:554-567.

Smeds, K.A. et al., "Photocrosslinkable polysaccharides for in situ hydrogel formation," J. Biomed. Mater. Res. (2001) 54:115-121.

Smejkalova, D. et al., "Structural and conformational differences of acylated hyaluronan modified in protic and aprotic solvent system," Carbohydrate Polymers (2012) 87(2):1460-1466.

Staskus, P.W. et al., "Double-Stranded Structure for Hyaluronic Acid in Ethanol-Aqueous Solution as Revealed by Circular Dichroism of Oligomers," Biochemistry vol. 27, No. 5, 1988, pp. 1528-1534.

Svanovsky, E. et al., "The effect of molecular weight on the biodistribution of hyaluronic acid radiolabeled with 111-In after intravenous administration to rats," Fur. J. Drug Metab. Ph. 2008, vol. 33, No. 3, pp. 149-157.

Tan, H. et al., "Injectable in situ forming biodegradable chitosan-hyaluronic acid based hydrogels for cartilage tissue engineering," Biomaterials (2009) 30(13):2499-2506.

Tankam, P.F. et al., "Alkynyl polysaccharides: synthesis of propargyl potato starch followed by subsequent derivatizations," Carbohydrate Research (2007) 342:2049-2060.

Tao, Y. et al., "Core cross-linked hyaluronan-styrylpyridinium micelles as a novel carrier for paclitaxel," Carbohydrate Polymers (2012) 88(1):118-124.

Testa, G. et al., "Influence of dialkyne structure on the properties of new click-gels based on hyaluronic acid," International Journal of Pharmaceutics (2009) 378:86-92.

Fleige, E. et al., "Stimuli-responsive polymeric nanocarriers for the controlled transport of active compounds: Concepts and applications," Advanced Drug Delivery Reviews (2012) 64(9):866-884.

Funakoshi, T. et al., "Novel chitosan-based hyaluronan hybrid polymer fibers as a scaffold in ligament tissue engineering," Journal of Biomedical Materials Reasearch, Part A (2005) 74A(3):338-346.

Ghan, R. et al., "Enzyme-Catalyzed Polymerization of Phenols within Polyelectrolyte Microcapsules," Macromolecules (2004) 37(12), 4519-4524.

Gibby, W.A., "Cross-Linked DTPA Polysaccharides for Magnetic Resonance Imaging, Synthesis and Relaxation Properties," Invest. Radiol. 1989, vol. 24, pp. 302-309.

Gilabert, M.A. et al., "Differential substrate behaviour of phenol and aniline derivatives during oxidation by horseradish peroxidase: kinetic evidence for a two-step mechanism," Biochim. Biophys. Acta. (2004) 1699:235-243.

Gilabert, M.A. et al., "Kinetic characterization of phenol and aniline derivates as substrates of peroxidase," Biol. Chem. (2004) 385(9):795-800.

Gilabert, M.A. et al., "Stereospecificity of horseradish peroxidase," Biol. Chem. (2004) 385:1177-1184.

Godula, K. et al., "Synthesis of Glycopolymers for Microarray Applications via Ligation of Reducing Sugars to a Poly(acryloyl hydrazide) Scaffold," J. Am. Chem. Soc. (2010) 132:9963-9965.

Gong, J. et al., "Polymeric micelles drug delivery system in oncology," Journal of Controlled Release (2012) 159(3):312-323.

Guillaumie, F. et al., "Comparative studies of various hyaluronic acids produced by microbial fermentation for potential topical ophthalmic applications," Journal of Biomedical Materials Research Part A (2009) 1421-1430.

Gupta, P. et al., "Hydrogels: from controlled release to pH-responsive drug delivery," Drug Discovery Today (2002) 7(10):569-579.

Hasegawa, T. et al., "'Click chemistry' on polysaccharides: a convenient, general, and monitorable approach to develop (1-3)-ß-D-glucans with various functional appendages," Carbohydrate Research (2006) 341:35-40.

Hewson, W. D. et al., "Oxidation of p-cresol by horseradish peroxidase compound I," J Biol Chem 1976, 251 (19), 6036-42.

Hewson, W. D. et al., "Stoichiometry of the reaction between horseradish peroxidase and p-cresol," J Biol Chem 1976, 251(19), 6043-52.

Higashimura, H. et al., Oxidative Polymerization. John Wiley & Sons, Inc. Olefin Fibers (2002) 10:740-764.

Hocek, M., "Tvorba C-C A C-X Vazeb Cross-Coupling Reakcemi Katalyzovanymi Komplexy Rechodnych Kovu," Chem. Listy (2003) 97:1145-1150.

Hoffman, A.S., "'Intelligent' Polymers in Medicine and Biotechnology," Artificial Organs (1995) 19(5):458-467.

Hofmann, H. et al., "Conformational Changes of Hyaluronic Acid in Acid Medium," Albrecht Von Graefe's Archive for Clinical and Experimental Opthamology vol. 198, No. 1, 1976, pp. 95-100.

Holten, K.B. et al., "Appropriate Prescribing of Oral Beta-Lactam Antibiotics," American Family Physician (2000) 62(3):611-620.

Huang, G. et al., "Superparamagnetic Iron Oxide Nanoparticles: Amplifying ROS Stress to Improve Anticancer Drug Efficacy.," Theranostics (2013) 3(2):116-126.

Huerta-Angeles, G. et al., "Synthesis of highly substituted amide hyaluronan derivatives with tailored degree of substitution and their crosslinking via click chemistry," Carbohydrate Polymers (2011) 84:1293-1300.

Huh, K.M. et al., "Hydrotropic polymer micelle system for delivery of paclitaxel," Journal of Controlled Release (2005) 101:59-68.

Hynes, W.L. et al., "Hyaluronidases of Gram-positive bacteria," FEMS Microbiology Letters (2000) 183:201-207.

Inanaga, J. et al., "A Rapid Esterification by Means of Mixed Anhydride and Its Application to Large-ring Lactonization," Bulletin of the Chemical Society of Japan (1979) 52(7):1989-1993.

International Search Report in International Patent Application No. PCT/CZ2009/000131, dated Apr. 9, 2010, 3 pgs.

International Search Report in International Patent Application No. PCT/CZ2010/000030, dated Sep. 1, 2010, 3 pgs.

International Search Report in International Patent Application No. PCT/CZ2010/000128, dated Jun. 9, 2011, 3 pgs.

International Search Report in International Patent Application No. PCT/CZ2010/000129, dated Jun. 15, 2011, 3 pgs.

International Search Report in International Patent Application No. PCT/CZ2011/000126, dated Apr. 12, 2012, 3 pgs.

International Search Report in International Patent Application No. PCT/CZ2012/000035, dated Aug. 28, 2012, 3 pgs.

International Search Report in International Patent Application No. PCT/CZ2013/000023, dated Aug. 9, 2013, 3 pgs.

International Search Report in International Patent Application No. PCT/CZ2013/000057, dated Jul. 24, 2013, 4 pgs.

International Search Report in International Patent Application No. PCT/CZ2013/000063, dated Apr. 23, 2015, 7 pgs.

International Search Report in International Patent Application No. PCT/CZ2013/000091, dated Oct. 31, 2013, 3 pgs.

(56) References Cited

OTHER PUBLICATIONS

International Search Report in International Patent Application No. PCT/CZ2013/000116, dated Jan. 28, 2014, 4 pgs.
International Search Report in International Patent Application No. PCT/CZ2013/000155, dated Feb. 19, 2014, 4 pgs.
International Search Report in International Patent Application No. PCT/CZ2013/000156, dated Apr. 4, 2014, 5 pgs.
International Search Report in International Patent Application No. PCT/CZ2013/000157, dated Mar. 19, 2014, 3 pgs.
International Search Report in International Patent Application No. PCT/CZ2013/000158, dated Mar. 19, 2014, 3 pgs.
International Search Report in International Patent Application No. PCT/CZ2014/000138, dated May 4, 2015, 4 pgs.
International Search Report in International Patent Application No. PCT/CZ2015/000018, dated Jul. 22, 2015, 5 pgs.
International Search Report in International Patent Application No. PCT/CZ2015/000068, dated Jan. 8, 2016, 4 pgs.
International Search Report in International Patent Application No. PCT/CZ2016/000027, dated Jun. 27, 2016, 3 pgs.
Jacoboni, I., "Hyaluronic Acid by Atomic Force Microscopy," Journal of Structural Biology vol. 126, 1999, pp. 52-58.
Jahn, M. et al., "The reaction of hyaluronic acid and its monomers glucuronic acid and N-acetylglucosamine, with reactive oxygen species," Carbohydrate Research, 1999, vol. 321, pp. 228-234.
Japanese Official Action (English language translation) in Japanese Patent Application No. 2012-542355, dated Oct. 17, 2014.
Japanese Official Action (English language translation) in Japanese Patent Application No. 2014-506754, dated Jan. 22, 2015, 2 pgs.
Japanese Official Action (including English language translation) in Japanese Patent Application No. 2012-542356, dated Oct. 3, 2014, 8 pages.
Jia, X.Q. et al., "Synthesis and Characterization of in Situ Cross-Linkable Hyaluronic Acid-Based Hydrogels with Potential Application for Vocal Fold Regeneration," Macromolecules (2004) 37:3239-3248.
Jiang, B. et al., "Study on Tempo-mediated selective oxidation of hyaluronan and the effects of salt on the reaction kinetics," Carbohydrate Research, Pergamon, GB (2000) 327(4)455-461.
Office Action in U.S. Appl. No. 15/038,078, dated Nov. 3, 2017, 10 pgs.
Jin, R. et al., "Enzyme-mediated fast in situ formation of hydrogels from dextran-tyramine conjugates," Biomaterials (2007) 28(18):2791-2800.
Job, D. et al., "Substituent effect on the oxidation of phenols and aromatic amines by horseradish peroxidase compound I," Eur J Biochem 1976, 66 (3), 607-14.
Jou, Chi-Hsiung et al., "Biocompatibility and Antibacterial Activity of Chitosan and Hyaluronic Acid Immobilized Polyester Fibers," Journal of Applied Polymer Science vol. 104, No. 1, 2007, pp. 220-225.
Juhlin, L., "Hyaluronan in skin," Journal of Internal Medicine (1997) 242:61-66.
Kalyanaraman, B. et al., "Peroxidatic oxidation of catecholamines. A kinetic electron spin resonance investigation using the spin stabilization approach" Journal of Biological Chemistry (1984) 259(12)"7584-7589.
Katritzky, A.R. et al., "Cycloaddition Reactions of Heteroaromatic Six-Membered Rings," Chem. Rev. (1989) 39:827-861.
Kawaguchi, Y. et al., "The relation between the adsorption behavior at the interface and the conformational changes in hyaluronates partially modified with various acyl chains," Carbohydrate Polymers (1995) 26:149-154.
Kedar, U. et al., "Advances in polymeric micelles for drug delivery and tumor targeting," Nanomedicine: Nanotechnology, Biology, and Medicine (2010) 6(6):714-729.
Kim, B. et al., "Complexation Phenomena in pH-Responsive Copolymer Networks with Pendent Saccarides," Macromol. (2002) 35:9545-9550.
Kim, T.G. et al., "Controlled Release of Paclitaxel from Heparinized Metal Stent Fabricated by Layer-by-Layer Assembly of Polylysine and Hyaluronic Acid-g-Poly(lactic-co-glycolic acid) Micelles Encapsulating Paclitaxel," Biomacromolecules (2009) 10(6):1532-1539.
Korsmeyer, R.W. et al., "Mechanisms of solute release from porous hydrophilic polymers," International Journal of Pharmaceutics (1983) 15:25-35.
Kumar, A. et al., "Development of hyaluronic acid-Fe2O3 hybrid magnetic nanoparticles for targeted delivery of peptides," Nanomedicine: Nanotechnology, Biology and Medicine, Elsevier, NL (2007) 3(2)132-137.
Kuo, J.W., "Practical Aspects of Hyaluronan Based Medical Products," 2006, CRC Press, Taylor & Francis Group, pp. 60-61.
Lapcik, L. Jr. et al., Chemicke Listy vol. 85, 1991, pp. 281-298.
Laurent, S. et al., "Magnetic fluid hyperthennia: Focus on superparamagnetic iron oxide nanoparticles," Advances in Colloid and Interface Science (2011) 166:8-23.
Leach, J.B. et al., "Characterization of protein release from photocrosslinkable hyaluronic acid-polyethylene glycol hydrogel tissue engineering scaffolds," Biomaterials (2005) 26:125-135.
Leach, J.B. et al., "Photocrosslinked Hyaluronic Acid Hydrogels: Natural, Biodegradable Tissue Engineering Scaffolds," Biotechnol Bioeng. (2003) 82:578-589.
Lee, Dong-Eun et al., "Amphiphilic hyaluronic acid-based nanoparticles for tumor-specific optical/MR dual imaging," Journal of Materials Chemistry (2012) 22(1):10444-10447.
Lee, F. et al., "An injectable enzymatically crosslinked hyaluronic acid-tyramine hydrogel system with independent tuning of mechanical strength and gelation rate," Soft Matter 2008, 4, 880-887.
Lee, F. et al., "An injectable hyaluronic acid-tyramine hydrogel system for protein delivery," Journal of Controlled Release (2009) 134:186-193.
Lee, K.Y. et al., "Electrospinning of polysaccharides for regenerative medicine," Advanced Drug Delivery Reviews (2009) 61:1020-1032.
Lee, S.A. et al., "Spectroscopic studies of the physical properties of hyaluronate films: the origin of the phase transition," Carbohydrate Polymers (1995) 28:61-67.
Lee, Yuhan et al., "Bioinspired Surface Immobilization of Hyaluronic Acid on Monodisperse Magnetite Nanocrystals for Targeted Cancer Imaging," Advanced Materials (2008) 20:4154-4157.
Li, J. et al., "Electrospinning of Hyaluronic Acid (HA) and HA/Gelatin Blends," Macromolecular Rapid Communications (2006) 27:114-120.
Li, J. et al., "Redox-sensitive micelles self-assembled from amphiphilic hyaluronic acid-deoxycholic acid conjugates for targeted intracellular delivery of paclitaxel," Biomaterials (2012) 33(7):2310-2320.
Li, M. et al., Comparison of Two Ultrasmall Superparamagnetic Iron Oxides on Cytotoxicity and MR Imaging of Tumors, Theranostics (2012) 2(1):76-85.
Linhardt, R.J. et al., "Polysaccharide lyases," Applied Biochemistry and Biotechnology (1986) 12:135-176.
Linhartova, B., Nanovlakna na bazi hyaluronanu, Bakalarska prace, Vysoke uceni technicke v Brne, 2008 (English language Abstract on p. 3).
Liu, Yanchun et al., "Biocompatibility and stability of disulfide-crosslinked hyaluronan films," Biomaterials (2005) 26(23):4737-4746.
Liu, Yanhua et al., "Dual targeting folate-conjugated hyaluronic acid polymeric micelles for paclitaxel delivery," International Journal of Pharmaceutics (2011) 421(1):160-169.
Luo, Y. et al., "Novel amphoteric pH-sensitive hydrogels derived from ethylenediaminetetraacetic dianhydride, butanediamine and amino-terminated poly(ethylene glycol): Design, synthesis and swelling behavior," European Polymer Journal (2011) 47:40-47.
Maeda, H., "The Enhanced Permeability and Retention (EPR) Effect in Tumor Vasculature: The Key Role of Tumor-Selective Macromolecular Drug Targeting," Advances in Enzyme Regulation (2001) 41(1):189-207.
Malkoch, M. et al., "Synthesis of well-defined hydrogel networks using Click chemistry," Chem. Commun. (2006) 2774-2776.
Marega, R. et al., "Hyaluronan-Carbon Nanotube Derivatives: Synthesis, Conjugation with Model Drugs, and DOSY NMR Characterization," Eur. J. Org. Chem. (2011) 28:5617-5625.

(56) References Cited

OTHER PUBLICATIONS

Matsushima, R. et al., "Photoreactions of Alkylated 2-Pyridones," J. Chem. Soc. Perkin Trans. 2 (1985) 1445-1448.
Mayol, L. et al., "Amphiphilic hyaluronic acid derivatives toward the design of micelles for the sustained delivery of hydrophobic drugs," Carbohydrate Polymers (2014) 102:110-116.
Mazzone, S.B., "Fluorescent styryl dyes FM 1-43 and FM2-10 are muscarinic receptor antagonists: intravital visualization of receptor occupancy," The Journal of Physiology (2006) 575(1):23-35.
McIntyre, J.E., "The Chemistry of Fibres," Studies in Chemistry No. 6, 1971, p. 15.
McTaggart, L.E. et al., "Assessment of polysaccharide gels as drug delivery vehicles," Int. J. Pharm. 1993, vol. 100, pp. 199-206.
Merriam Webster Online Dictionary, obtained online at: http://www.merriam-webster.com/cgi-bin/dictionary?book=Dictionary&va=derivative, downloaded on Jul. 5, 2008.
Milas, M. et al., "Characterization and Properties of Hyaluronic Acid (Hyaluronan)," Polysaccharides: Structural Diversity and Functional Versatility, by S. Dumitriu 1998, Marcel Dekker Inc., pp. 535-549.
Miller, R.J. et al., Chemistry and Biology of Hyaluronan : Medicinal Uses of Modified Hyaluronate. Elsevier Ltd. 2004. 505-528.
Nevell, T.P. et al., "Cellulose Chemistry and its Applications," 1985, John Wiley & Sons, pp. 455-479.
Office Action in U.S. Appl. No. 13/512,484, dated May 11, 2016, 8 pgs.
Office Action in U.S. Appl. No. 13/512,484, dated Oct. 1, 2015, 8 pgs.
Office Action in U.S. Appl. No. 13/512,484, dated Sep. 11, 2014, 8 pgs.
Office Action in U.S. Appl. No. 13/514,759, dated Jul. 30, 2015, 12 pgs.
Office Action in U.S. Appl. No. 13/514,759, dated Sep. 24, 2014, 10 pgs.
Office Action in U.S. Appl. No. 13/977,181, dated Jan. 22, 2016, 8 pgs.
Office Action in U.S. Appl. No. 14/113,527, dated Feb. 12, 2016, 11 pgs.
Akkara, J.A. et al., "Synthesis and Characterization of Polymers Produced by Horseradish Peroxidase in Dioxane," Journal of Polymer Science Part A: Polymer Chemistry (1991) 29(11):1561-1574.
Aldrich, Chem Files Synthetic Methods Oxidation, May 2005, vol. 5, No. 1 pp. 1-11 (English language translation included).
Angelin, M. et al., "Direct, Mild, and Selective Synthesis of Unprotected Dialdo-Glycosides," European Journal of Organic Chemistry (2006):4323-4326.
Armstrong, D.C. et al., "Culture Conditions Affect the Molecular Weight Properties of Hyaluronic Acid Produced by *Streptococcus zooepidemicus*," Appl. Environ. Microbiol. (1997) 63(7):2759-2764.
Atkins, E.D.T. et al., "The Conformation of the Mucopolysaccharides," J. Biochem. (1972) 128:1255-1263.
Atkins, E.D.T. et al., "The Molecular Structure of Hyaluronic Acid," Biochemical Journal (1971) 125(4):92.
Author unknown, "Readily Accessible 12-I-51 Oxidant for the Conversion of Primary and Secondary Alcohols to Aldehydes and Ketones," Journal of Organic Chemistry, 1983, vol. 84, pp. 4155-4156.
Author unknown, Encyclopedia of Cellulose, Asakura Publishing Co., Ltd., pp. 155-156 (Nov. 10, 2000).
Bakke, M. et al., "Identification, characterization, and molecular cloning of a novel hyaluronidase, a member of glycosyl hydrolase family 16, from *Penicillium* spp.," FEBS Letters (2011) 585(1):115-120.
Banerji, S. et al., "Structures of the Cd44-hyaluronan complex provide insight into a fundamental carboxyhydrate-protein interaction," Nature structural and molecular biology (2007) 14:234-239.
Benedetti, L. et al., "Biocompatibility and biodegradation of different hyaluronan derivatives (Hyaff) implanted-in rats," Biomaterials (1993) 14(15):1154-1160.

Bezakova, Z. et al., "Effect of microwave irradiation on the molecular and structural properties of hyaluronan," Carbohydrate Polymers (2008) 73(4):640-646.
Boyer, I.J., "Toxicity of dibutyltin, tributyltin and other organotin compounds to humans and to experimental animals," Toxicology (1989) 55(3), 253-298.
Buffa, R. et al., "Branched hyaluronic acid, synthesis, analysis and biological properties," Journal of Tissue Engineering and Regenerative Medicine (2014) 8(1):321.
Buffa, R. et al., "New method of immobilization of hyaluronic acid oligomers," Journal of Tissue Engineering and Regenerative Medicine (2014) 8(1):321-322.
Burdick, J.A. et al., "Controlled Degradation and Mechanical Behavior of Photopolymerized Hyaluronic Acid Networks," Biomacromolecules (2005) 6:386-391.
Burdick, J.A. et al., "Hyaluronic Acid Hydrogels for Biomedical Applications," Adv. Mater. (2011) 23:H41-H56.
Burke, J., Solubility Parameters: Theory and Application, the Book and Paper Group Annual, vol. Three, 1984, 62 pgs.
Burner, U. et al., "Transient-state and steady-state kinetics of the oxidation of aliphatic and aromatic thiols by horseradish peroxidase," FEBS Letters (1997) 411(2-3):269-274.
Chem Files Synthetic Methods Oxidation, May 2005, vol. 5, No. 1 pp. 1-11.
Chen, L. et al., "Synthesis and pH sensitivity of carboxymethyl chitosan-based polyampholyte hydrogel for protein carrier matrices," Biomaterials (2004) 25:3725-3732.
Cornwell, M.J. et al., "A One-Step Synthesis of Cyclodextrin Monoaldehydes," Tetrahedron Letters (1995) 36(46):8371-8374.
Crescenzi, V. et al., "Novel Hydrogels via Click Chemistry: Synthesis and Potential Biomedical Applications," Biomacromolecules (2007) 8:1844-1850.
Czech Official Action in Czech Patent Application No. PV 2008-705, dated Oct. 23, 2009, 2 pgs.
Czech Official Action in Czech Patent Application No. PV 2009-835, dated Aug. 2010, 2 pgs.
Czech Official Action in Czech Patent Application No. PV 2009-836, dated Aug. 6, 2010, 2 pgs.
Czech Search Report in Czech Patent Application No. PV 2010-1001, dated Sep. 27, 2011, 1 pg.
Czech Search Report in Czech Patent Application No. PV 2011-241, dated Nov. 30, 2011, 1 pg.
Czech Search Report in Czech Patent Application No. PV 2012-136, dated Sep. 18, 2012, 3 pgs.
Czech Search Report in Czech Patent Application No. PV 2012-282, dated Jan. 30, 2013, 1 pg.
Czech Search Report in Czech Patent Application No. PV 2012-306, dated Feb. 11, 2013, 1 pg.
Czech Search Report in Czech Patent Application No. PV 2012-664, dated May 24, 2013, 3 pgs.
Czech Search Report in Czech Patent Application No. PV 2012-842, dated Aug. 19, 2013, 3 pgs.
Czech Search Report in Czech Patent Application No. PV 2012-843, dated Aug. 20, 2013, 1 pg.
Darr, A. et al., "Synthesis and characterization of tyramine-based hyaluronan hydrogels," Journal of Materials Science: Materials in Medicine (2009) 20(1), 33-44.
Dilling, W.L. et al., "Organic Photochemistry. XII. The Photodimerization and Photoisomerization of 2-Pyridone and Its Monochloro Derivatives," Mol. Photochem. (1973) 5(4):371-409.
Ding, B. et al., "Tempo-mediated selective oxidation of substituted polysaccharides—an efficient approach for the determination of the degree of substitution at C-6," Carbohydrate Research (2008) 343(18)3112-3116.
Donati, A. et al., "Solution Structure of Hyaluronic Acid Oligomers by Experimental and Theoretical NMR, and Molecular Dynamics Simulation," Biopolymers vol. 59, 2001, pp. 434-445.
Duncan, R. et al., "Nanomedicine(s) under the Microscope," Molecular Pharmaceutics (2011) 8(6):2101-2141.
Dunford, H. B. et al., "Kinetics of the oxidation of p-aminobenzoic acid catalyzed by horseradish peroxidase compounds I and II," J Biol Chem 1975, 250(8), 2920-32.

(56) References Cited

OTHER PUBLICATIONS

Eenschooten, C. et al., "Preparation and structural characterisation of novel and versatile amphiphilic octenyl succinic anhydride-modified hyaluronic acid derivatives," Carbohydrate Polymers (2010) 79(3):597-605.
El-Dakdouki, M.H. et al., "Development of drug loaded nanoparticles for tumor targeting. Part 1: synthesis, characterization, and biological evaluation in 2D cell cultures," Nanoscale (2013) 5(9):3895-3903.
El-Dakdouki, M.H. et al., "Development of Multifunctional Hyaluronan-Coated Nanoparticles for Imaging and Drug Delivery to Cancer Cells," Biomacromolecules (2012) 13(4):1144-1151.
El-Sherbiny, I.M. et al., "Poly(ethylene glycol)-carboxymethyl chitosan-based pH-responsive hydrogels: photo-induced synthesis, characterization, swelling, and in vitro evaluation as potential drug carriers," Carbohydrate Research (2010) 345:2004-2012.
Elander, R.P., "Industrial production of ß-lactam antibiotics," Applied Microbiology and Biotechnology (2003) 61:385-392.
European First Official Action in European Patent Application No. 10812840.6-1306, dated Jul. 2, 2013, 4 pgs.
European Second Official Action in European Patent Application No. 10812840.6-1306, dated Sep. 24, 2014, 5 pgs.
Feng, Qian et al., "Self-Assembly Behaviour of Hyaluronic Acid on Mica by Atomic Force Microscopy," vol. 20, No. 1, 2004, pp. 146-148 and 152 (English language Abstract p. 152).
Ferrero, C. et al., "Fronts movement as a useful tool for hydrophilic matrix release mechanism elucidation," International Journal of Pharmaceutics (2000) 202:21-28.
Ferruti, P. et al., "Novel Poly(amido-amine)-Based Hydrogels as Scaffolds for Tissue Engineering," Macromol. Biosci. (2005) 5:613-622.
Thakar, D. et al., "A quartz crystal microbalance method to study the terminal functionalization of glycosaminoglycans," Chemical Communications (2014) 50(96):15148-15151.
Til, H.P. et al., "Acute and Subacute Toxicity of Tyramine, Spennidine, Spennine, Putrescine and Cadaverine in Rats," Food and Chemical Toxicology (1997) 35(3-4):337-348.
Tonelli, A.E., "Effects of crosslink density and length on the number of intramolecular crosslinks (defects) introduced into a rubbery network," Polymer (1974) 15(4):194-196.
Tornoe, C. et al., "Peptidotriazoles on Solid Phase: [1,2,3]-Triazoles by Regiospecific Copper(I)-Catalyzed 1,3-Dipolar Cycloadditions of Terminal Alkynes to Azides," J. Org. Chem. (2002) 67:3057-3064.
Um, I.C. et al., "Electro-Spinning and Electro-Blowing of Hyaluronic Acid," Biomacromolecules (2004) 5:1428-1436.
Uyama, H. et al., "Enzymatic Synthesis of Polyphenols," Current Organic Chemistry (2003) 7:1387-1397.
Van Bommel, K.J.C. et al., "Responsive Cyclohexane-Based Low-Molecular-Weight Hydrogelators with Modular Architecture," Angew. Chem. Int. Ed. (2004) 1663-1667.
Veitch, N.C., "Horseradish peroxidase: a modern view of a classic enzyme," Phytochemistry (2004) 65:249-259.
Wang, J. et al., "Polymeric Micelles for Delivery of Poorly Soluble Drugs: Preparation and Anticancer Activity in Vitro of Paclitaxel Incorporated into Mixed Micelles Based on Poly(ethylene Glycol)-Lipid Conjugate and Positively Charged Lipids," Journal of Drug Targeting (2005) 13(1):73-80.
Wang, X. et al., "Formation of water-resistant hyaluronic acid nanofibers by blowing-assisted electro-spinning and non-toxic post treatments," Polymer (2005) 46:4853-4867.
Weng, L. et al., "In vitro and in vivo suppression of cellular activity by guanidinoethyl disulfied released from hydrogel microspheres composed of partially oxidized hyaluronan and gelatin," Biomaterials, Aug. 3, 2008, vol. 29, pp. 4149-4156.
Weng, L. et al., "Self-crosslinkable hydrogels composed of partially oxidized hyaluronan and gelatin: in vitro and in vivo responses," Journal of Biomedical Materials Research Part A, Aug. 9, 2007, pp. 352-365.
Wermuth, C.G., "Similarity in drugs: reflections on analogue design," Drug Discovery Today (2006) 11(7/8):348-354.
Won, K. et al., "Horseradish Peroxidase-Catalyzed Polymerization of Cardanol in the Presence of Redox Mediators," Biomacromolecules (2003) 5(1), 1-4.
Wondraczek, H. et al., "Synthesis of highly functionalized dextran alkyl carbonates showing nanosphere formation," Carbohydrate Polymers (2011) 83:1112-1118.
Written Opinion in International Patent Application No. PCT/CZ2009/000131, dated Apr. 9, 2010, 3 pgs.
Written Opinion in International Patent Application No. PCT/CZ2010/000030, dated Sep. 1, 2010, 4 pgs.
Written Opinion in International Patent Application No. PCT/CZ2010/000128, dated Jun. 9, 2011, 4 pgs.
Written Opinion in International Patent Application No. PCT/CZ2010/000129, dated Jun. 15, 2011, 4 pgs.
Written Opinion in International Patent Application No. PCT/CZ2011/000126, dated Apr. 12, 2012, 4 pgs.
Written Opinion in International Patent Application No. PCT/CZ2012/000035, dated Aug. 28, 2012, 4 pgs.
Written Opinion in International Patent Application No. PCT/CZ2013/000023, dated Aug. 9, 2013, 3 pgs.
Written Opinion in International Patent Application No. PCT/CZ2013/000057, dated Jul. 24, 2013, 4 pgs.
Written Opinion in International Patent Application No. PCT/CZ2013/000063, dated Apr. 23, 2015, 9 pgs.
Written Opinion in International Patent Application No. PCT/CZ2013/000091, dated Oct. 31, 2013, 4 pgs.
Written Opinion in International Patent Application No. PCT/CZ2013/000116, dated Jan. 28, 2014, 5 pgs.
Written Opinion in International Patent Application No. PCT/CZ2013/000155, dated Feb. 19, 2014, 6 pgs.
Written Opinion in International Patent Application No. PCT/CZ2013/000156, dated Apr. 4, 2014, 7 pgs.
Written Opinion in International Patent Application No. PCT/CZ2013/000157, dated Mar. 19, 2014, 6 pgs.
Written Opinion in International Patent Application No. PCT/CZ2013/000158, dated Mar. 19, 2014, 7 pgs.
Written Opinion in International Patent Application No. PCT/CZ2014/000138, dated May 4, 2015, 5 pgs.
Written Opinion in International Patent Application No. PCT/CZ2015/000018, dated Jul. 22, 2015, 8 pgs.
Written Opinion in International Patent Application No. PCT/CZ2015/000068, dated Jan. 8, 2016, 6 pgs.
Written Opinion in International Patent Application No. PCT/CZ2016/000027, dated Jun. 27, 2016, 6 pgs.
Xu, Y.-P. et al., "Kinetics of Phenolic Polymerization Catalyzed by Peroxidase in Organic Media," Biotechnology and Bioengineering (1995) 47(1):117-119.
Yamane, Shintaro et al., "Feasibility of chitosan-based hyaluronic acid hybrid biomaterial for a novel scaffold in cartilage tissue engineering," Biomaterials (2005) 26(6);611-619.
Yao, F. et al., "A Novel Amphoteric, pH-Sensitive, Biodegradable Poly[chitosan-g-(L-lactic-co-citric) acid] Hydrogel," Journal of Applied Polymer Science (2003) 89:3850-3854.
Yeom, J. et al., "Effect of Cross-Linking Reagents for Hyaluronic Acid Hydrogel Dermal Fillers on Tissue Augmentation and Regeneration," Bioconjugate Chemistry (2010) 21(2):240-247.
Zeng, J. et al., "Photo-Induced Solid-State Crosslinking of Electrspun Poly(vinyl alcohol) Fibers," Macromolecular Rapid Communications (2005) 26:1557-1562.
Zhong, S.P. et al., "Biodegradation of hyaluronic acid derivatives by hyaluronidiase," Biomaterials (1994) 15(5):359-365.
Aubry-Rozier, B., Revue Medicale Suisse (2012) 14:571.
Baeurle, S.A. et al., "Effect of the counterion behavior on the frictional-compressive properties of chondroitin sulfate solutions," Polymer (2009) 50(7):1805-1813.
Baijal, K. P. et al., "Tumor-enhancing effects of cholic acid are exerted on the early stages of colon carcinogenesis via induction of aberrant crypt foci with an enhanced growth phenotype," Canadian Journal of Physiology and Pharmacology, 1998, 76(12), 1095-1102.
Balan, V. et al., "Strategies to improve chitosan hemocompatibility: A review," European Polymer Journal (2004) 53:171-188.

(56) References Cited

OTHER PUBLICATIONS

Bobula, T. et al., "One-pot synthesis of alpha,beta-unsaturated polyaldehyde of chondroitin sulfate," Carbohydrate Polymers (2016) 136:1002-1009.
Bobula, T. et al., "Solid-state photocrosslinking of hyaluronan microfibres," Carbohydrate Polymers (2015) 125:153-160.
Bottegoni, C. et al., "Oral chondroprotection with nutraceuticals made of chondroitin sulphate plus glucosamine sulphate in osteoarthritis," Carb. Pol. (2014) 109:126-138.
Brand-Williams, W. et al., "Use of a Free Radical Method to Evaluate Antioxidant Activity," LWT-Food Science and Technology (1995) 28:25-30.
Breunig, M. et al., "Breaking up the correlation between efficacy and toxicity for nonviral gene delivery," PNAS (2007) 104(36):14454-14459.
Carey, F.A. et al., Advanced Organic Chemistry Part A: Structure and Mechanisms, Plenum Press, New York and London, pp. 475-479 (1990).
Cayman Chemical, Stearic Acid, obtained online at: https://www.caymanchem.com/pdfs/10011298.pdf, p. 1. (Year: 2017).
Chen, H. et al., "A dual-targeting nanocamer based on modified chitosan micelles for tumor imaging and therapy," Polym. Chem. 2014, 5, 4734-4746.
Sherrick, G. R. et al., "Indocyanine Green: Observations on Its Physical Properties, Plasma Decay, and Hepatic Extraction," J.Clinical Investigation, 1960, 39, 592-600.
Choi, K. Y. et al., "Self-assembled hyaluronic acid nanoparticles as a potential drug carrier for cancer therapy: synthesis, characterization, and in vivo biodistribution," J. Mater. Chem. 2009, 19 (24), 4102-4107.
Choi, K. Y. et al., "Self-assembled hyaluronic acid nanoparticles for active tumor targeting," Biomaterials 2010, 31 (1), 106-114.
Choi, W. II et al., "Targeted antitumor efficacy and imaging via multifunctional nano-carrier conjugated with anti-HER2 trastuzumab, Nanomedicine: Nanotechnology, Biology, and Medicine (2015) 11:359-368.
Chu et al., "Electro-Spinning and Electro-Blowing of Hyaluronic Acid," 2004, Biomacromolecules, vol. 5, pp. 1428-1436. (Year: 2004).
Collins, M. N. et al., "Hyaluronic Acid Based Scaffolds for Tissue Engineering—a review," Carbohydrate Polymers (2013) 92:1262-1279.
Contipro, Specialty Hyaluronan Chemicals Product Catalog, 52 pgs. (retrieved on Sep. 26, 2018). (Year: 2018).
Cumpstey, I., Review Article "Chemical Modification of Polysaccharides," ISRN Organic Chemistry (2013) Article ID 417672, 27 pgs.
D'Este, M. et al., "A systematic analysis of DMTMM vs EDC/NHS for ligation of amines to Hyaluronan in water," Carbohydr. Polym. 2014, 108, 239-246.
Dawlee, S. et al., "Oxidized Chondroitin Sulfate-Cross-Linked Gelatin Matrixes: A New Class of Hydrogels," Biomacromolecules (2005) 6(4):2040-2048.
De Figueiredo, R.M. et al., "N,N'-Carbonyldiimidazole-Mediated Cyclization of Amino Alcohols to Substituted Azetidines and Other N-Heterocycles," J. Org. Chem. (2006) 71(11):4147-4154.
Frangioni, J. V., "In vivo near-infrared fluorescence imaging," Curr. Opin. Chem. Biol. (2003) 7(5):626-634.
Funfstuck, V. V. et al., "Kontaktallergie gegenuber Dicyclohexylcarbodiimid," Dermatosen (1986) 34(4):110-111.
Furuta, T. et al., "Anthraquinon-2-ylmethoxycarbonyl (Aqmoc): A New Photochemically Removable Protecting Group for Alcohols," Org. Lett. (2001) 3(12):1809-1812.
Gobouri, A.A. et al., "Novel Synthesis of Diketo-Acid Chondroitin-4-sulfate as Coordination Biopolymer Precursor through Oxidation of Chondroitin-4-sulfate by Alkaline Permanganate," International Journal of Sciences (2013) 7:1-11.
Green, T.W. et al., "Protective Groups in Organic Synthesis," 1999, New York: John Wiley & Sons, 3rd ed., Chap. 1, pp. 1-16.

Hacker, M. C. et al., "Multi-Functional Macromers for Hydrogel Design in Biomedical Engineering and Regenerative Medicine," Inter. J. of Mol. Sc. (2015) 16:27677-27706.
Hassan, R. et al., "Kinetics and mechanism of oxidation of chondroitin-4-sulfate polysaccharide by chromic acid in aqueous perchlorate solutions," (2013) Carbohydrate Polymers 92:2321-6.
Hill, T. K. et al., "Indocyanine Green-Loaded Nanoparticles for Image-Guided Tumor Surgery," Bioconjugate Chem. (2015) 26:294-303.
Horton, D. et al., "Synthesis of 2,3-Unsaturated Polysaccharides From Amylose and Xylan," Carbohydrate Research (1975) 40:345-352.
Huang, L. et al., "A Facsimile Method for Oxidation of Primary Alcohols to Caroxylic Acids and Its Application in Glycosaminoglycan Syntheses," Chemistry (2006) 12(20):5246-5252.
Huerta-Angeles, G. et al., "Novel synthetic method for the preparation of amphiphilic hyaluronan by means of aliphatic aromatic anhydrides," Carbohydrate Polymers (2014) 111:883-891.
Hussain, M. A. et al., "Acylation of Cellulose with N,N'-Carbonyldiimidazole-Activated Acids in the Novel Solvent Dimethyl Sulfoxide/Tetrabutylammonium Fluoride," Macromol. Rapid Commun. (2004) 25:916-920.
International Search Report in International Patent Application No. PCT/CZ2016/000065, dated Sep. 30, 2016, 5 pgs.
International Search Report in International Patent Application No. PCT/CZ2016/000071, dated Oct. 10, 2016, 4 pgs.
International Search Report in International Patent Application No. PCT/CZ2016/050036, dated Feb. 6, 2017, 4 pgs.
International Search Report in International Patent Application No. PCT/CZ2016/050048, dated May 3, 2017, 4 pgs.
International Search Report in International Patent Application No. PCT/CZ2017/050026, dated Oct. 26, 2017, 2 pgs.
International Search Report in International Patent Application No. PCT/EP2016/064653, dated Aug. 25, 2016, 4 pgs.
Japanese Official Action in Japanese Patent Application No. 2015-543316, 5 pgs.
Ji, Y. et al., "Electrospun three-dimensional hyaluronic acid nanofibrous scaffolds," Biomaterials (2006) 27(1):3782-3792.
Katz, S.A. et al., "The Toxicology of Chromium with Respect to its Chemical Speciation: a Review," Journal of Applied Toxicology (1993) 13(3):217-224.
Kelly, S. J. et al., "Kinetic properties of *Streptococcus pneumoniae* hyaluronate lyase," Glycobiology (2001) 11(4):297-304.
Khetan, S. et al., "Patterning network structure to spatially control cellular remodeling and stem cell fate within 3-dimensional hydrogels," Biomaterials (2010) 31(32):8228-8234.
Khetan, S. et al., "Sequential crosslinking to control cellular spreading in 3-dimensional hydrogels," Soft Matter (2009) 5:1601-1606.
Klan, P. et al., "Photoremovable Protecting Groups in Chemistry and Biology: Reaction Mechanisms and Efficacy," Chem. Rev. (2013) 113(1):119-191.
Kobayashi, H. et al., "New Strategies for Fluorescent Probe Design in Medical Diagnostic Imaging," Chem. Rev. (2010) 110(5):2620-2640.
Kokuryo, D. et al., "Corrigendum to SPIO-PICsome: Development of a highly sensitive and stealth-capable MRI nano-agent for tumor detection using SPIO-loaded unimellar polyion complex vesicles (PICsomes)," Journal of Controlled Release (2014) 178:125.
Khademhosseini, A. et al., "Layer-by-layer deposition of hyaluronic acid and poly-L-lysine for patterned cell co-cultures," Biomaterials (2004) 25:3583-3592.
Mondek, J. et al., "Thermal degradation of high molar mass hyaluronan in solution and in powder; comparison with BSA," Polymer Degradation and Stability (2015) 120:107-113.
Schachter, D., "The Source of Toxicity in CTAB and CTAB-Stabilized Gold Nanorods," MS thesis submitted to Graduate School—New Brunswick Rutgers, the State University of New Jersey and the Graduate School of Biomedical Sciences, University of Medicine and Dentistry of New Jersey, 2013, 70 pgs.
Kühn, A. V. et al., "Identification of hyaluronic acid oligosaccharides by direct coupling of capillary electrophoresis with electrospray ion trap mass spectrometry," Rapid Communications in Mass Spectrometry (2003) 17:576-582.

(56) References Cited

OTHER PUBLICATIONS

Lee, Dong-Eun et al., "Hyaluronidase-Sensitive SPIONs for MR/Optical Dual Imaging Nanoprobes," Marcomol. Res. (2011) 19(8):861-867.
Liang, Y. et al., "An in situ formed biodegradable hydrogel for reconstruction of the corneal endothelium," Colloids and Surfaces B: Biointerfaces (2011) 82(1):1-7.
Luo, S. et al., "A review of NIR dyes in cancer targeting and imaging," Biomaterials (2011) 32:7127-7138.
Mero, A. et al., "Hyaluronic Acid Bioconjugates for the Delivery of Bioactive Molecules," Polymers (2014) 6(2):346-369.
Miki, K. et al., "Near-Infrared Dye-Conjugated Amphiphilic Hyaluronic Acid Derivatives as a Dual Contrast Agent for in Vivo Optical and Photoacoustic Tumor Imaging," Biomacromolecules (2015) 16:219-227.
Nimmo, C. M. et al., "Diels-Alder Click Cross-Linked Hyaluronic Acid Hydrogels for Tissue Engineering," Biomacromolecules (2011) 12:824-830.
Normandin, L. et al., "Manganese Neurotoxicity: An Update of Pathophysiologic Mechanisms," Metab Brain Dis (2002) 17(4):375-387.
Office Action in U.S. Appl. No. 14/647,626, dated Nov. 13, 2017, 18 pgs.
Office Action in U.S. Appl. No. 14/647,649, dated Apr. 19, 2018, 9 pgs.
Office Action in U.S. Appl. No. 14/647,649, dated Dec. 8, 2017, 9 pgs.
Office Action in U.S. Appl. No. 15/038,078, dated Dec. 21, 2018, 9 pgs.
Office Action in U.S. Appl. No. 15/038,078, dated Mar. 1, 2018, 10 pgs.
Office Action in U.S. Appl. No. 15/038,078, dated Sep. 11, 2018, 9 pgs.
Office Action in U.S. Appl. No. 15/124,827, dated Dec. 7, 2017, 9 pgs.
Office Action in U.S. Appl. No. 15/322,776, dated Apr. 17, 2018, 27 pgs.
Office Action in U.S. Appl. No. 15/322,776, dated Dec. 10, 2018, 31 pgs.
Office Action in U.S. Appl. No. 15/737,894, dated Oct. 5, 2018, 27 pgs.
Pasqui, D. et al., "Polysaccharide-Based Hydrogels: The Key Role of Water in Affecting Mechanical Properties," Polymers (2012) 4:1517-1534.
Perale, G. et al., "Hydrogels in Spinal Cord Injury Repair Strategies," ACS Chem. Neurosci. (2011) 2(7):336-345.
Piggot, A.M. et al., "Synthesis of a new hydrophilic o-nitrobenzyl photocleavable linker suitable for use in chemical proteomics," Tetr. Lett. (2005) 46(47):8241-8244.
Price, Richard D. et al., "Hyaluronic acid: the scientific and clinical evidence," J. Plast. Reconstr. Aesthet. Surg. (2007) 60(10):1110-1119.
Rowe et al., "Handbook of Pharmaceutical Excipients," 6th edition, 2009, Pharmaceutical Press, pp. 110-114 and 581-585. (Year: 2009).
Saettone et al., "Evaluation of muco-adhesive properties and in vivo activity of ophthalmic vehicles based on hyaluronic acid," 1989, International Journal of Pharmaceutics, vol. 51, pp. 203-212. (Year: 1989).
Su, W.Y. et al., "Injectable oxidized hyaluronic acid/adipic acid dihydrazide hydrogel for nucleus pulposus regeneration," Acta. Biomater. (2010) 6(8):3044-3055.
Tan, X. et al., "A NIR heptamethine dye with intrinsic cancer targeting, imaging and photosensitizing propeties," Biomaterials (2012) 33:2230-2239.
Thelin, M. et al., "Biological functions of iduronic acid in chondroitin/dermatan sulfate," FEBS Journal (2013) 280:2431-2446.
Thomas, R. G. et al, "Hyaluronic acid conjugated superparamagnetic iron oxide nanoparticle for cancer diagnosis and hyperthermia therapy," Carbohydrate Polymers 131 (2015) pp. 439-446.
Vigo, T. L. et al., "Deoxycelluloses and Related Structures," Polymers for Advanced Technologies (1999) 10:311-320.
Wang, W. et al., "Developing Fluorescent Hyaluronan Analogs for Hyaluronan Studies," Molecules 2012, 17, 1520-1534.
Weng L., et al., "Self-crosslinkable hydrogels composed of partially oxidized hyaluronan and gelatin: In vitro and in vivo responses," Journal of Biomedical Materials Research Part A, 85:352-365.
Werner, T. et al., "Simple Method for the Preparation of Esters from Grignard Reagents and Alkyl 1-Imidazolecarboxylates," J. Org. Chem. (2006) 71(11):4302-4304.
Written Opinion in International Patent Application No. PCT/CZ2016/000065, dated Sep. 30, 2016, 5 pgs.
Written Opinion in International Patent Application No. PCT/CZ2016/000071, dated Oct. 10, 2016, 5 pgs.
Written Opinion in International Patent Application No. PCT/CZ2016/050036, dated Feb. 6, 2017, 6 pgs.
Written Opinion in International Patent Application No. PCT/CZ2016/050048, dated May 3, 2017, 6 pgs.
Written Opinion in International Patent Application No. PCT/CZ2017/050026, dated Oct. 26, 2017, 5 pgs.
Written Opinion in International Patent Application No. PCT/EP2016/064653, dated Aug. 25, 2016, 6 pgs.
Xu, Y. et al., "Feasibility study of a novel crosslinking reagent (alginate dialdehyde) for biological tissue fixation," Carbohydrate Polymers (2012) 87(2):1589-1595.
Yang, Rui-Meng et al., "Hylauronan-modified superparamagnetic iron oxide nanoparticles for bimodal breast cancer imaging and photothermal therapy," Int'l J. of Nanomedicine 2017: 12, pp. 197-206.
Ye, Y. et al., "Integrin Targeting for Tumor Optical Imaging," Theranostics 2011, 1, 102-126.
Ye, Y. et al., "Multivalent Carbocyanine Molecular Probes: Synthesis and Applications," Bioconjugate Chem. 2005, 16, 51-61.
Ye, Y. et al., "Novel Near-Infrared Fluorescent Integrin-Targeted DFO Analogue," Bioconjugate Chem. (2008) 19:225-234.
Ye, Y. et al., "Polyvalent Carbocyanine Molecular Beacons for Molecular Recognitions," J. Am. Chem. Soc. 2004, 126, 7740-7741.
Zaafarany, I. et al., "Oxidation of Some Sulfated Carbohydrates: Kinetics and Mechanism of Oxidation of Chondroitin-4-Sulfate by Alkaline Permanganate with Novel Synthesis of Coordination Biopolymer Precursor," J. Mat. Sci. Res. (2013) 2(4):23-36.
Zeng, Yuan-Xian et al., "Preparation and Enhancement of Thermal Conductivity of Heat Transfer Oil-Based MoS2 Nanofluids," Journal of Nanomaterials, vol. 2013, Art. ID 270490, 6 pgs.
Zou, X.H. et al., "Specific interactions between human fibroblasts and particular chondroitin sulfate molecules for wound healing," Acta Biomaterialia (2009) 5(5):1588-1595.
Drury, J. L. et al., "The tensile properties of alginate hydrogels," Biomaterials 25 (2004) 3187-3199.
Hannemann, T. et al., "Polymer-Nanoparticle Composites: From ynthesis to Modem Applications," Materials 2010, 3, 3468-3517.
Morfa, A. J. et al., "Comparison of biodegradable substrates for printed organic electronic devices," Cellulose (2016) 23:3809-3817.
Nazri, N. A. M. et al., "A facile modification approach for polyacrylonitrile-based UF hollow fiber membrane utilizing polyacrylonitrile-g-poly(vinyl alcohol) graft copolymer," J Polym Res (2014) 21:594.
Oprea, S., "Preparation and characterization of the agar/polyurethane composites," Journal of Composite Materials 45(20) 2039-2045.
Wang, M. et al., Photo-pattemable, stretchable and electrically conductive graft copolymers of poly(3-hexylthiophene), Polym. Chem., 2019, 10, 6278.
Zia, K. M. et al, "Molecular engineering of chitin based polyurethane elastomers," Carbohydrate Polymers 74 (2008) 149-158.
Zia, F. et al., "Glucomannan based polyurethanes: A critical short review of recentadvances and future perspectives," International Journal of Biological Macromolecules 87 (2016) 229-236.
Yuk, H. et al., "Skin-inspired hydrogel-elastomer hybrids with robust interfaces and functional microstructures," Nature Communications, 2016, pp. 1-11.

* cited by examiner

SELF-SUPPORTING, BIODEGRADABLE FILM BASED ON HYDROPHOBIZED HYALURONIC ACID, METHOD OF PREPARATION AND USE THEREOF

FIELD OF THE ART

The invention relates to a self-supporting biodegradable film based on hydrophobized hyaluronic acid, method of preparation thereof and use thereof, especially in medical applications thanks to its controlled solubility, biodegradability, surface morphology, mechanical and other properties.

PRIOR ART

Hyaluronic acid or a salt thereof (HA) is a linear polysaccharide, which is composed of repeating disaccharide units formed by glucuronic acid, which is bonded by β-1, 3-glycosidic bond to N-acetyl-glucosamine.

It is a substance which naturally occurs in the organism, where it is a part of the extracellular matrix, acts as a lubricant in joints, eyes and the like. It also interacts with cell receptors, whereby it is able to regulate the cells. Thanks to its properties, HA is predetermined for use in various medical applications (Necas, Bartosikova et al. 2008). Since HA dissolves very rapidly in an aqueous environment or in body fluids, it is necessary to modify it for a number of applications. There are numerous types of modifications, e.g., the preparation of a soluble form of HA derivatized by tyramine, which upon the addition of crosslinking agents forms an insoluble hydrogel network (Calabro, Darr et al. 2004, Wolfova, Pravda et al. 2013). The solubility of the HA chain may also be reduced by bonding hydrophobic groups thereto (Valle and Romeo 1987, Smejkalova, Huerta-Angeles et al. 2014, Ščudlová, Běťák et al. 2014). Such a derivative is then insoluble in aqueous media and soluble mostly in a mixture of water and an organic solvent (depending on the degree of substitution by the hydrophobic chain, combined with the molecular weight).

The international patent application No. WO2014082609 (Smejkalova, Huerta-Angeles et al. 2014) relates to the preparation of hydrophobized hyaluronic acid as a carrier of biologically active hydrophobic substances. The hydrophobization of hyaluronan is carried out by an esterification reaction of hyaluronan with a long chain carboxylic acid, wherein the activation is carried out by means of 2,4,6-trichlorobenzoic acid (TCBA) or another organic chloride.

One of the interesting application forms of hydrophobized hyaluronan is the preparation of thin films for external or internal use. Films that are applicable in medical applications are known, e.g., Seprafilm was used for the prevention of adhesions in repeated laparotomy. Seprafilm is a transparent adhesion bather composed of two anionic polysaccharides, HA and carboxymethyl cellulose, which were crosslinked together by 1-(3-dimethyl aminopropyl)-3-ethyl carbodiimide hydrochloride (EDC) (Altuntas, Kement et al. 2008, Beck 2008).

On the experimental basis, several films containing HA were prepared, e.g., Luo, Kirker et al. (2000). Also some patent documents disclose the preparation of a film made of insoluble or crosslinked hyaluronan, optionally hyaluronan in a mixture with another polymer (Becker, Dayton et al. 1996, Beck 2008). A hyaluronan layer was used also in the patent document No. CN202822230, where, however, it was not a self-supporting film, and further, only native hyaluronan was mentioned. Native hyaluronan together with leci-thin, which was added to enhance the hydrophobicity, was described in the article (Bialopiotrowicz, Jańczuk et al. 2006). Another film, used among others for the preparation of an antiadhesive barrier is a film made of an epoxide derivative of hyaluronan, which is prepared by precipitation in an organic solvent (EP2644623).

The films according to the patent application No. US20100092545 are prepared from water-soluble or insoluble polymers, preferably from polyethylene oxide, the anticipated use thereof is an alternative of oral drug forms. For that reason, it is very important that the distribution of the drug is homogeneous (the variation among the samples up to 10%) and that during the preparation, no aggregation and redistribution of the drug occur. This is achieved especially by the polymer being dosed in a high viscosity (which may be further increased by the addition of other substances such as alginate, carrageenan, guar gum and others), and stabilizers may be added as well, which prevent the aggregation and migration of the drug. Moreover, a part of the solvent must be removed during the first 10 minutes so that a viscoelastic film forms from the polymer solution, in which no migration or aggregation can proceed, according to the authors. This is achieved by applying a high temperature, which, however, in the case of hyaluronan and the derivatives thereof cannot be used since it would lead to the degradation of the film. In US20100092545, the authors do not discuss the resulting appearance of the film, which is affected by the adhesion of the film to the substrate during the drying and after the drying. The roughness of the film surface is not determined and influenced either. The film properties that could be modulated in this way, such as the swelling capacity and degradation rate, are not disclosed in the document. Regarding the intended application, the authors prefer the films to dissolve in an aqueous environment.

The patent document No. JP06025306 discloses a synthesis of highly substituted acylated hyaluronan derivatives and the use thereof for the preparation of fibres and films. The synthesis includes the preparation of a suspension of the polysaccharide in an organic acid. Since it is a suspension, the polysaccharide is not perfectly dissolved in the system, whereby causing inhomogeneous reactions and loss of compatibility of the polysaccharide in the system. The authors state that the reaction is catalysed by a super acid—in this case by superelectrophilic trifluoroacetic acid anhydride, which reacts vigorously with water. Therefore, there is a high risk in the case of industrial processes. Residues of trifluoroacetic acid, which is formed by anhydride hydrolysis when in contact with air humidity, may be present in the products and pose a significant danger when using the derivatives in biomedical applications (Maeda N. et al., 2014). Moreover, chlorinated solvents are used in the synthesis of the derivative, the use thereof FDA does not recommend in medical devices due to a high risk of the transfer of their residues into the fibres and films. The patent document mentions the preparation of fibres and films just in general terms and it does not deal with the determination of the properties thereof.

According to another US patent application No. US20120088832, the preparation of a porous film based on hyaluronan and alginate is disclosed, wherein the film should be used in medicine, especially as an antiadhesive preparation. The film is a crosslinked interpenetrating network of a porous character. In the Examples of the said document, nothing is mentioned about the swelling, biodegradation, solubility of the film and the determination of the residual solvents is not included.

To prepare films, the patent document No. EP0216453 used hydrophobized hyaluronan with esterified carboxylic groups of glucuronic acid, which were thus blocked and inaccessible for the binding on the CD44 receptor. Low-molecular or aromatic alcohols were used for the esterification. The method for preparing a self-supporting film includes dissolving a HA ester in dimetylsulfoxide (DMSO), applying it on a glass after the dissolution, the glass is immersed in ethanol which extracts DMSO (the film is not soluble in ethanol) and then the film is peeled off the glass substrate, washed with ethanol, water and again with ethanol. The resulting film is dried for 48 hours at 30° C. in a compression device.

The patent document No. US20040192643 also mentions films made of hydrophobized hyaluronan, preferably a benzoyl HA derivative. Again, substitution on carboxyl is carried out, where in order to achieve the insolubility of hyaluronan 80 to 100% of all carboxyl groups of HA are blocked. The method of film preparation corresponds to the already mentioned method disclosed in EP216453 above. However, the drying takes place at 63° C. for 30 minutes in vacuum.

By means of DMSO extraction into another solvent, uncontrollable surface defects may form, which could be unacceptable in some applications. Moreover, in case it is necessary to use an extraction solvent, a low concentration of residual solvents in the final product cannot be guaranteed. Furthermore, there is no mention of mechanical, physical or biological properties of the films in the above mentioned documents Nos. EP0216453 and US20040192643.

The patent document No. WO2010137374 discloses a self-supporting polymer permeable membrane comprising a block copolymer, in which hydrophilic polymer and hydrophobic polymer components are covalently bonded, wherein the hydrophilic polymer component forms perpendicularly oriented cylindrical structures and the hydrophobic polymer component is crosslinkable. Therefore, the membrane is composed of a covalently crosslinked block copolymer. There is no mention of hyaluronic acid. As far as the process of preparation of said membrane is concerned, the presence of the so-called "sacrificing layer" is necessary, which is present on the substrate. The solution of the block polymer is applied on the "sacrificing layer", wherein after the solvent is evaporated the hydrophobic polymer component of the block copolymer is photo-crosslinked, and then the "sacrificing layer" must be removed from the resulting membrane by means of dissolution, preferably in a solvent in which the membrane itself is insoluble.

As mentioned above, the drawbacks of the up-to-now known films based on hyaluronic acid include especially their multiple-step complicated preparation. Other known processes of film preparation cannot be used for hyaluronan and derivatives thereof. The authors of some patents or patent applications do not mention any possibility to affect the solubility, swelling and biodegradability of the film, which is desirable in applications in medical devices. The appearance of the film and the mechanical properties thereof may be influenced by the repetitive contact with the solvent in the case of the process according to EP0216453 or US20040192643 (ethanol, by means of which DMSO is extracted, is a precipitation agent of hyaluronan). Further, e.g., DMSO is used, which cannot be removed within an acceptable time limit by means of drying. Another drawback is the use of large numbers of solvents, which leads to a higher probability of the presence of residual solvents in the product. Some processes use, besides hyaluronan, also other polymers in order to increase the insolubility of the final material, or to influence the properties of the initial polymer solution.

SUMMARY OF THE INVENTION

The above drawbacks of the prior art are overcome by the self-supporting film based on hyaluronic acid ester according to the invention, the subject-matter of which lies in that it comprises a $C_{10}$-$C_{22}$-acylated hyaluronic acid derivative according to the general formula (I)

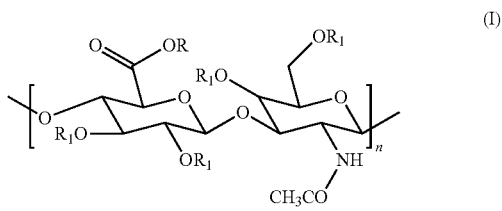

wherein R is $H^+$ or $Na^+$, and wherein $R^1$ is H or —C(=O)$C_xH_y$, wherein x is an integer within the range from 9 to 21 and y is an integer within the range from 11 to 43, preferably 19 to 43, and $C_xH_y$ is a linear or branched, saturated or unsaturated $C_9$-$C_{21}$ chain, wherein at least in one repeating unit one or more $R^1$ is —C(=O)$C_xH_y$, and where n is within the range from 12 to 4000, preferably 250 to 4000, more preferably 250 to 2500, the most preferably 250 to 1000. Preferably, the film according to the invention comprises palmitoyl hyaluronan, because palmitic acid is degraded in the body by means of β-oxidation of fatty acids. Moreover, the film according to the invention preferably comprises lauroyl hyaluronan.

The film according to the invention comprises $C_{10}$-$C_{22}$ acylated hyaluronan derivative (i.e., hydrophobized hyaluronan), wherein one or more bonds in $C_{10}$-$C_{22}$ acyls may be unsaturated and wherein the $C_{10}$-$C_{22}$ acyl is preferably bonded only on the primary alcohol in the position 6 of N-acetyl glucosamine. Therefore, carboxylic groups are not modified, their retention is necessary for the interactions of hyaluronan with the CD44 receptor, which intermediates the interaction, adhesion and migration of the cells and which also participates in the interaction of the cell with hyaluronan. It was proven that the higher the substitution degree of the hyaluronan carboxyl, the worse the process of interaction of the cells with hyaluronan is (Qiu, Li et al. 2014). From this point of view, it is advantageous not to carry out the modification of the carboxyl and to focus on other reaction sites, which are primary and/or secondary alcohol groups, especially where there is the requirement of higher substitution degrees, which are necessary for most applications.

The film according to the invention prepared from $C_{10}$-$C_{22}$-acylated hyaluronic acid derivative according to formula I above is non-cytotoxic with respect to cells, is biocompatible and biodegradable, even in case of using a highly substituted derivative (including 100% substitution degree by the acyl). For applications in medicine, where there is the prerequisite that the film will be mechanically stressed (antiadhesive barriers, tissue engineering etc.), it is more preferable to use a form which is insoluble in aqueous media, i.e., a film according to the invention, instead of the covalently crosslinked form that is often fragile upon swelling. The film according to the invention forms a resistant elastic membrane upon hydration, which can be subjected to a mechanical stress to a certain degree (by means of elongation, bending, compression).

The films are non-cytotoxic with respect to cells (in vitro testing).

According to a preferred embodiment of the invention, the film comprises acylated derivatives of hyaluronic acid, having the molecular weight from $1\times10^5$ to $1\times10^6$ g/mol, preferably from $1\times10^5$ to $5\times10^5$ g/mol, more preferably from $2\times10^5$ to $3\times10^5$ g/mol.

According to another preferred embodiment of the invention, the film comprises acylated derivatives of hyaluronic acid, having the substitution degree within the range from 15 to 160%, preferably 50 to 100%, more preferably 80 to 100%.

The substitution degree of 100% means that every primary alcoholic group (—C6) of the hyaluronan dimer is substituted by one aliphatic chain. The substitution degree above 100% means that besides every primary alcoholic group (—C6) of the dimer, also some secondary alcoholic groups (—C4 on N-acetylglucosamine or —C2 or —C3 on glucuronic acid) are randomly substituted.

Surprisingly, it was found out that the film according to the invention is biodegradable even in case of using a derivative having a high substitution degree, which is between 80 to 100%, and even up to 160%.

According to another preferred embodiment of the invention, the film has the thickness within the range from 2 to 100 μm, preferably within the range from 5 to 25 μm and the Young's modulus within the range from 1 to 5000 MPa in the dry state, preferably within the range from 500 to 5000 MPa, more preferably from 1000 to 3000 MPa.

In the case of dry non-hydrated films according to the invention, the Young's modulus is independent of the substitution degree, the substituent and the molecular weight of HA. In the hydrated state, it is very difficult to quantify the Young's modulus due to technical masons, however, visual tests enable to evaluate that with the decreasing molecular weight the toughness of the film decreases, the film becomes more fragile. Also, with an increasing substitution degree, the Young's modulus in the hydrated state is increasing.

According to another preferred embodiment of the invention, the surface roughness RMS (root mean square) of at least one of the film surfaces is within the range from 0.5 to 100 μm, preferably within the range from 0.5 to 2 nm.

According to another preferred embodiment of the invention, the film may comprise biologically active substances which are selected from the group comprising pharmaceutically and cosmetically active substances, preferably vitamins, drugs, preferably cytostatics, steroids, further phytoextracts, phytocomplexes or phytoactive substances and the like.

The unique features of the film according to the invention are: 1) the film is composed of hydrophobized hyaluronan only, 2) no synthetic polymers are used, 3) the film does not comprise any toxic solvents, 4) the eventual residual solvents are non-toxic and are below the limits for medical use, 5) the swelling capacity and solubility of the film can be controlled by modifying the substitution degree of hyaluronan, 6) the film degradation rate can be controlled by modifying the substitution degree of hyaluronan, 7) the film is not deformed on the surface and the thickness thereof is homogeneous, 8) the surface appearance of the film can be controlled, 9) the mechanical properties of the film can be controlled, especially in the hydrated form thereof, 10) the RMS roughness of at least one of the film surfaces may be below 2 nm, 11) the film thickness can be controlled, 12) the film is non-adherent for cells, 13) the film does not comprise the so-called "skin surface". The "skin surface" is a surface crust due to which the film would deform, twist and under which bubbles could form. It forms during the drying of a polymer solution in air when often a layer of highly concentrated polymer appears near the surface. This layer possesses significantly different rheological properties with respect to the rest of the film. The drying of the film according to the invention proceeds in such a way that the film is not open to its surroundings (it is being dried in a closed space), and consequently it is being dried more slowly and a higher tension of solvent vapours exists above the solution. Such arrangement helps to prevent the formation of the surface crust. Surprisingly, it was found out that even in case the humidity in the closed space during the film drying was low, the surface crust did not form.

No residues of hydrophobization agents that could originate in the substrate on which the film is being prepared have been found in the films according to the invention.

Compared to the prior art processes, the method of preparation of the film according to the invention is very simple and it consists in dissolving the hydrophobized hyaluronan (of any disclosed molecular weight and of any disclosed substitution degree) in the respective solvent, applying the respective amount thereof on a defined substrate, and evaporating the solvent in an arrangement where there is a higher vapour tension of the solvent above the solution being dried in a closed space. The solvent evaporation is carried out either by means of free evaporation of the solvent or by heating the lower surface of the film lying on the substrate while heating or cooling the upper surface of the film (drying in a temperature gradient and in a closed space). Therefore, the method of preparation of the film according to the invention is very cheap and simple. It is also important that the surface of the film according to the invention is very smooth (RMS up to 2 nm) on the side adjoining to the substrate (i.e., the lower surface of the film). The opposite side of the film (i.e., the upper surface of the film) is rougher depending on the drying conditions and on the type of the derivative.

According to another aspect, the invention further relates to the method of preparation of the film according to the invention which consists in that a solution comprising a $C_{10}$-$C_{22}$-acylated hyaluronic acid derivative according to the general formula (I) above in a mixture of water and $C_1$-$C_6$ alcohol, preferably ethanol or propan-2-ol, is prepared, which is stirred, then it is applied on a substrate and dried in a closed space, whereupon it is removed from the substrate.

According to another preferred embodiment of the method according to the invention, the amount of the $C_{10}$-$C_{22}$-acylated hyaluronic acid derivative in the solution is within the range from 0.5 to 3 wt. %, the content of the $C_1$-$C_6$ alcohol, preferably ethanol or propan-2-ol, is within the range from 25 to 55 vol. % and the content of water in the solution is within the range from 45 to 75 vol. %. The prepared solution has a relatively low viscosity whereby the formation of bubbles at stirring and dosing the solution is prevented.

According to another preferred embodiment of the method according to the invention, the solution is stirred for 20 to 72 hours, preferably 20 to 48 hours.

According to another preferred embodiment of the method according to the invention, the drying of the film is carried out in a closed space at the temperature of 20° C. to 50° C., preferably 30° C. to 40° C.; for 3 to 6 hours, preferably 4 to 5 hours.

According to another preferred embodiment of the method according to the invention, the drying of the film is carried out in a temperature gradient, which is performed by heating the lower surface of the film lying on the substrate to a temperature which is higher by at least 1° C. than the temperature to which the opposite upper surface of the film is heated or cooled. Preferably, the lower surface of the film lying on the substrate is heated to a temperature within the range from 20° C. to 60° C. and the opposite upper surface of the film is heated or cooled to a temperature within the range from 10° C. to 59° C. More preferably, the lower surface of the film lying on the substrate is heated to the temperature of 50° C. and the opposite upper surface of the film is cooled to the temperature of 20° C. When applying the temperature gradient, the film is being dried in a closed space.

According to another preferred embodiment of the method according to the invention, the solution is dried in the temperature gradient for 6 to 12 hours, preferably 6 hours.

The advantage of the preparation of the film according to the invention is the fact that the film is insoluble in aqueous media and that it is formed only by the acylated hyaluronan according to the general formula I defined above, without the necessity of adding crosslinking agents and of further treatment. The film according to the invention also comprises a high amount of dry matter, preferably more than 85%.

The solution of the acylated hyaluronan derivative used for the preparation of films according to the invention may be preferably modified in various ways, biologically active substances may be mixed into the solution, the biologically active substances being selected from the group comprising pharmaceutically and cosmetically active substances, preferably vitamins, drugs, preferably cytostatics, steroids, further phytoextracts, phytocomplexes or phytoactive substances and the like.

According to another preferred embodiment of the method according to the invention, the substrate is a polymer selected from the group comprising polyvinyl alcohol, polypropylene, polyethylene, polyoxymethylene or polystyrene. Moreover, the substrate may be hydrophobized glass. In a preferred embodiment, hydrophobized glass is used. The contact wetting angle of the substrate surface by demi water is within the range from 30° to 120°, preferably 50° to 70°.

The advantage of the above disclosed method according to the invention is, beside the simplicity thereof, also the possibility of preparing a film having a very smooth surface from the side of the substrate (i.e., with a very smooth lower surface of the film) by choosing a suitable substrate that is very smooth itself.

The possibility of influencing the deformation and the overall appearance of the film appears to be very useful, the influencing being effected by affecting the adhesion (interaction) of the polymer solution, the drying and the dried film to the substrate on which the solution is applied and on which the drying takes place. It is preferred that the polymer film is fully adhered to the substrate, it does not spontaneously peel off and, at the same time, that the film may be removed from the substrate just by applying minimal strength.

A good wettability of the substrate surface by the polymer solution is the first stage of adhesion. The adhesion of the drying and the dried film according to the invention to the substrate and thus the appearance of the film can be influenced by the selection of a substrate having various wettabilities of the surface, expressed by the contact angle. For each type of the derivative (different modification, different molecular weight and different substitution degree), a substrate having a totally specific value of wettability may be preferably used. In case of well adhered films their surface is flat after they are peeled off, in case of less adhered films or non-adhering films the surface thereof is more or less deformed or shrank. Preferably, hydrophobized glass is used as the substrate.

The film is prepared by evaporating a mixture of an organic solvent (typically $C_1$-$C_6$ alcohol) with water. The surface of the thus prepared film has the surface appearance and the RMS roughness controlled by the selection of optimal solvents, derivative, drying conditions and the substrate and may be prepared as transparent. The film thickness is from 2 to 100 μm, preferably from 5 to 25 μm. Since the film is prepared on a substrate the wettability of which may be modulated, the adhesion of the film to the substrate and thus also the morphology of the film surface may be influenced.

The preparation of the film proceeds in the following manner: the solution of an acylated hyaluronan derivative having a relatively low viscosity, after having been stirred sufficiently, is applied on a suitable substrate and is dried. The low viscosity of the solution that is applied on the substrate prevents the formation of bubbles when stirring and dosing the solution. Then the film is removed from the substrate. The drying time ranges from 5 to 12 hours, depending on the volume and concentration of the solution and further on the set temperatures and the solvent used. The film comprises less than 0.02% of the solvent, e.g., ethanol or propan-2-ol, whereby safely fulfilling the requirements on the amount of the residual solvents for medical use. Such material may be used for the construction of a medical device. The advantage of the method of preparation of such a film according to the invention is that the film is insoluble in aqueous media and is composed only of the modified hyaluronan, without the necessity of adding crosslinking agents and of further treatment.

The film according to the invention can be used according to the invention, e.g., for the production of antiadhesive barriers and for other applications in human and veterinary medicine. The degradation of the film in the human body can be modulated by the molecular weight of the derivative used and by the substitution degree of hyaluronan by the akyl, and ranges between several hours and several months. The acylated hyaluronan derivatives, as well as the films prepared therefrom, are degradable in vitro.

The swelling capacity of the film, or the solubility thereof, is also controlled by the molecular weight of the derivative used and by the substitution degree of the hyaluronan chain by the $C_{10}$-$C_{22}$ akyl.

It is important that as opposed to the derivatives disclosed in the prior art patent documents, the film according to the invention comprises only the $C_{10}$-$C_{22}$-acylated hyaluronic acid derivative that has retained all of its carboxylic groups of glucuronic acid, which are the groups being responsible for the biological properties of hyaluronan.

Another aspect of the invention is the influencing of the surface appearance of the film by means of influencing the adhesion of the dried polymer to the substrate on which the film is prepared. The result thereof may be a very flat film without creasing or shrinking.

According to yet another embodiment, the film according to the invention, as defined above, is used in medical applications, biotechnology applications or as a support for the deposition of active components. Preferably, it is used for the construction of a medical device, such as antiadhesive barriers, since cells do not adhere thereto. Further, the preferred medical applications in which the film according to the invention may be used include, for example, medical pharmaceutical applications, such as the treatment of chronic and acute wounds, or, e.g., dental applications.

Definitions of the Terms

The term "substitution degree" means the number of $C_{10}$-$C_{22}$ acyls bound to 100 hyaluronan dimers. For example, the substitution degree of 20% means that 20 of each 100 hyaluronan dimers are substituted by $C_{10}$-$C_{22}$ acyls. During the substitution, the hydrogen atom on the primary hydroxyl group of N-acetyl-glucosamine or on the secondary OH groups of glucuronic acid is substituted by a $C_{10}$-$C_{22}$ acyl.

The term "film" means a self-supporting thin polymer sheet, a planar structure.

The term "film area" means the area of the film calculated from the dimensions thereof (in m²).

The term "medical device" means an aid usable by itself or in combination with any accessories for a specific use for diagnostic or medical purposes, such as an antiadhesive barrier.

The term "closed space" means a space in which the drying of the film is carried out at a specific temperature or in a temperature gradient and which is closed without the free access of ambient air.

The term "conditioned medium" means a THP-1 (human monocyte cancer cell line) conditioned medium, which is a standard RPMI medium (Roswell Park Memorial Institute medium) enriched with 10% fetal bovine serum in which human cell line THP-1 cells were cultured continuously for 7 days. The THP-1 cells are used as a model of human monocytes and they produce, besides a number of growth factors and cytokines, also enzymes causing the degradation of extracellular matrix components, especially matrix metalloproteinases, hyaluronidases or esterases. Before using or freezing, the medium was centrifuged and filtered through 0.22 μm filter in order to ensure purity and sterility.

EXAMPLES

Figure 1:
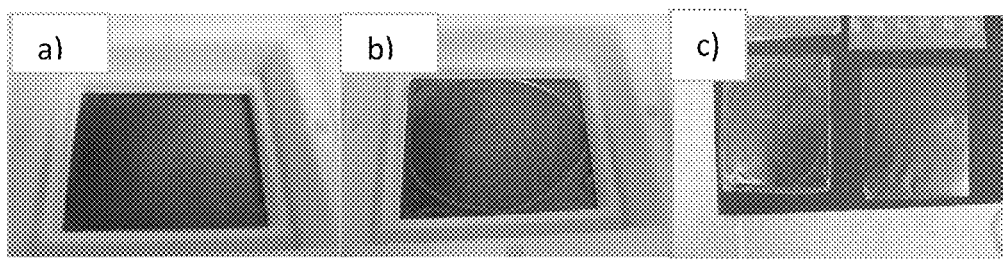
FIG. 1: effect of the adhesion of the film (a,b) on the basis of the oleyl derivative of sodium hyaluronate on the surface appearance thereof (c)

Example 1. Preparation of the Film Based on Palmitoyl Derivative of Sodium Hyaluronate 100 mg of palmitoyl derivative of sodium hyaluronate having the substitution degree of 100% and molecular weight $2.8 \times 10^5$ g/mol were dissolved in 20 ml of 55% solution of propan-2-ol and stirred for at least 72 hours. After stirring, the solution was dosed on a hydrophobized glass having the wettability by demi water of 61° (+/−2°) and dried in a closed space, in a temperature gradient at the temperature of the lower plate 50° C. and the temperature of the upper plate 40° C. for 12 hours. After drying, the film was evaluated, removed from the hydrophobized glass and characterized. The thickness of the thus prepared film was determined to be about 15 μm. The dry matter was determined to be around 92%.

Example 2. Preparation of the Film Based on Palmitoyl Derivative of Sodium Hyaluronate 100 mg of palmitoyl derivative of sodium hyaluronate having the substitution degree of 100% and molecular weight $2.12 \times 10^5$ g/mol were dissolved in 20 ml of 55% solution of propan-2-ol and stirred for at least 48 hours. After stirring, the solution was dosed on a hydrophobized glass having the wettability by demi water of 61° (+/−2°) and dried in a closed space, in a temperature gradient at the temperature of the lower plate 50° C. and the temperature of the upper plate 20° C. for 6 hours. After drying, the film was evaluated, removed from the hydrophobized glass and characterized. The thickness of the thus prepared film was determined to be about 15 μm.

Example 3. Preparation of the Film Based on Palmitoyl Derivative of Sodium Hyaluronate 100 mg of palmitoyl derivative of sodium hyaluronate having the substitution degree of 55% and molecular weight $6.0 \times 10^5$ g/mol were dissolved in 20 ml of 50% solution of ethanol and stirred for at least 20 hours. After stirring, the solution was dosed on a polyethylene substrate having the wettability by demi water of 79° (+/−4°) and dried in a closed space, in a temperature gradient at the temperature of the lower plate 30° C. and the temperature of the upper plate 29° C. for 12 hours. After drying, the film was evaluated, removed from the substrate and characterized. The thickness of the thus prepared film was determined to be about 15 μm.

Example 4. Preparation of the Film Based on Palmitoyl Derivative of Sodium Hyaluronate 50 mg of palmitoyl derivative of sodium hyaluronate having the substitution degree of 31% and molecular weight $9.9 \times 10^5$ g/mol were dissolved in 20 ml of 45% solution of ethanol and stirred for at least 20 hours. After stirring, the solution was dosed on a hydrophobized glass having the wettability by demi water of 61° (+/−2°) and dried in a closed space by evaporating the solvent at the temperature of 30° C. for 4 hours. After drying, the film was evaluated, removed from the substrate and characterized. The thickness of the thus prepared film was determined to be about 8 μm.

Example 5. Preparation of the Film Based on Palmitoyl Derivative of Sodium Hyaluronate 100 mg of palmitoyl derivative of sodium hyaluronate having the substitution degree of 20% and molecular weight $2.4 \times 10^5$ g/mol were dissolved in 20 ml of 25% solution of ethanol and stirred for at least 20 hours. After stirring, the solution was dosed on a polystyrene substrate having the wettability by demi water of 102° (+/−4°) and dried in a closed space, in a temperature gradient at the temperature of the lower plate 50° C. and the temperature of the upper plate 20° C. for 12 hours. After drying, the film was evaluated, removed from the substrate and characterized. The thickness of the thus prepared film was determined to be about 15 μm.

Example 6. Preparation of the Film Based on Erucoyl Derivative of Sodium Hyaluronate 100 mg of erucoyl derivative of sodium hyaluronate having the substitution degree of 160% and molecular weight $2.04 \times 10^5$ g/mol were dissolved in 20 ml of 60% solution of propan-2-ol and stirred for at least 20 hours. After stirring, the solution was dosed on a polypropylene substrate having the wettability by demi water of 105° (+/−2°) and dried in a closed space by evaporating the solvent at the temperature of 50° C. for 3 hours. After drying, the film was evaluated, removed from the substrate and characterized. The thickness of the thus prepared film was determined to be about 15 μm.

Example 7. Preparation of the Film Based on Lauroyl Derivative of Sodium Hyaluronate 100 mg of lauroyl derivative of sodium hyaluronate having the substitution degree of 64% and molecular weight $3.2 \times 10^5$ g/mol were dissolved in 20 ml of 50% solution of propan-2-ol and stirred for at least 20 hours. After stirring, the solution was dosed on hydrophobized glass having the wettability by demi water of 50° (+/−3°) and dried in a closed space, in a temperature gradient at the temperature of the lower plate 50° C. and the temperature of the upper plate 20° C. for 6 hours. After drying, the film was evaluated, removed from the substrate and characterized. The thickness of the thus prepared film was determined to be about 15 μm.

Example 8. Preparation of the Film Based on Lauroyl Derivative of Sodium Hyaluronate 100 mg of lauroyl derivative of sodium hyaluronate having the substitution degree of 90% and molecular weight $1.88 \times 10^5$ g/mol were dissolved in 20 ml of 50% solution of propan-2-ol and stirred for at least 20 hours. After stirring, the solution was dosed on hydrophobized glass having the wettability by demi water of 61° (+/−2°) and dried in a closed space by evaporating the solvent at the temperature of 20° C. for 6 hours. After drying, the film was evaluated, removed from the substrate and characterized. The thickness of the thus prepared film was determined to be about 15 μm.

Example 9. Preparation of the Film Based on Oleyl Derivative of Sodium Hyaluronate 100 mg of oleyl derivative of sodium hyaluronate having the substitution degree of 20% and molecular weight $2.8 \times 10^5$ g/mol were dissolved in 20 ml of 50% solution of propan-2-ol and stirred for at least 20 hours. After stirring, the solution was dosed on a polyvinylchloride substrate having the wettability by demi water of 95° (+/−5°) and dried in a closed space, in a temperature gradient at the temperature of the lower plate 50° C. and the temperature of the upper plate 20° C. for 6 hours. After drying, the film was evaluated, removed from the substrate and characterized. The thickness of the thus prepared film was determined to be about 15 μm.

Example 10. Preparation of the Film Based on Oleyl Derivative of Sodium Hyaluronate 300 mg of oleyl derivative of sodium hyaluronate having the substitution degree of 20% and molecular weight $2.8 \times 10^5$ g/mol were dissolved in 20 ml of 30% solution of propan-2-ol and stirred for at least 20 hours. After stirring, the solution was dosed on hydrophobized glass having the wettability by demi water of 57° (+/−3°) and dried in a closed space, in a temperature gradient at the temperature of the lower plate 50° C. and the temperature of the upper plate 20° C. for 12 hours. After drying, the film was evaluated, removed from the substrate and characterized. The thickness of the thus prepared film was determined to be about 40 μm.

Example 11. Preparation of the Film Based on Oleyl Derivative of Sodium Hyaluronate 300 mg of oleyl derivative of sodium hyaluronate having the substitution degree of 20% and molecular weight $2.8 \times 10^5$ g/mol were dissolved in 20 ml of 30% solution of propan-2-ol and stirred for at least 20 hours. After stirring, the solution was dosed on hydrophobized glass having the wettability by demi water of 107° (+/−1°) and dried in a closed space, in a temperature gradient at the temperature of the lower plate 50° C. and the temperature of the upper plate 20° C. for 12 hours. After drying, the film was evaluated, removed from the substrate and characterized. The thickness of the thus prepared film was determined to be about 40 μm.

Example 12. Preparation of the Film Based on Caprinyl (C10) Derivative of Sodium Hyaluronate 100 mg of caprinyl (C10) derivative of sodium hyaluronate having the substitution degree of 87% and molecular weight $2.50 \times 10^5$ g/mol were dissolved in 20 ml of 50% ethanol and stirred for at least 20 hours. After stirring, the solution was dosed on hydrophobized glass having the wettability by demi water of 61° (+/−2°) and dried in a closed space, in a temperature gradient at the temperature of the lower plate 60° C. and the temperature of the upper plate 40° C. for 10 hours. After drying, the film was evaluated, removed from the substrate and characterized. The thickness of the thus prepared film was determined to be about 15 μm, the dry matter was determined to be around 92%. The swelling capacity of the film was determined to be more than 100% (variation of the film area was measured) in equilibrium state.

Example 13. Preparation of the Film Based on Behenoyl Derivative of Sodium Hyaluronate 100 mg of behenoyl derivative of sodium hyaluronate having the substitution degree of 16% and molecular weight $3.3 \times 10^5$ g/mol were dissolved in 20 ml of 50% solution of propan-2-ol and stirred for at least 20 hours. After stirring, the solution was dosed on a polypropylene substrate having the wettability by demi water of 105° (+/−2°) and dried in a closed space, in a temperature gradient at the temperature of the lower plate 50° C. and the temperature of the upper plate 20° C. for 6 hours. After drying, the film was evaluated, removed from the substrate and characterized. The thickness of the thus prepared film was determined to be about 15 µm.

Example 14. Preparation of the Film Based on Lauroyl Derivative of Sodium Hyaluronate 100 mg of lauroyl derivative of sodium hyaluronate having the substitution degree of 29% and molecular weight $1.88 \times 10^5$ g/mol were dissolved in 20 ml of 50% solution of propan-2-ol and stirred for at least 20 hours. After stirring, the solution was dosed on hydrophobized glass having the wettability by demi water of 61° (+/−2°) and dried in a closed space, in a temperature gradient at the temperature of the lower plate 50° C. and the temperature of the upper plate 20° C. for 7 hours. After drying, the film was evaluated, removed from the substrate and characterized. The thickness of the thus prepared film was determined to be about 15 µm.

Example 15. Preparation of the Film Based on Oleyl Derivative of Sodium Hyaluronate 100 mg of oleyl derivative of sodium hyaluronate having the substitution degree of 15% and molecular weight $2.8 \times 10^5$ g/mol were dissolved in 20 ml of 50% solution of propan-2-ol and stirred for at least 48 hours. After stirring, the solution was dosed on hydrophobized glass having the wettability by demi water of 61° (+/−2°) and dried in a closed space, in a temperature gradient at the temperature of the lower plate 50° C. and the temperature of the upper plate 20° C. for 12 hours. After drying, the film was evaluated, removed from the substrate and characterized. The thickness of the thus prepared film was determined to be about 15 µm.

Example 16. Preparation of the Film Based on Palmitoyl Derivative of Sodium Hyaluronate 100 mg of palmitoyl derivative of sodium hyaluronate having the substitution degree of 34% and molecular weight $2.67 \times 10^5$ g/mol were dissolved in 20 ml of 50% solution of ethanol and stirred for at least 48 hours. After stirring, the solution was dosed on hydrophobized glass having the wettability by demi water of 61° (+/−2°) and dried in a closed space, in a temperature gradient at the temperature of the lower plate 50° C. and the temperature of the upper plate 20° C. for 12 hours. After drying, the film was evaluated, removed from the substrate and characterized. The thickness of the thus prepared film was determined to be about 15 µm.

Example 17. Preparation of the Film Based on Palmitoyl Derivative of Sodium Hyaluronate 100 mg of palmitoyl derivative of sodium hyaluronate having the substitution degree of 60% and molecular weight $2.8 \times 10^5$ g/mol were dissolved in 20 ml of 50% solution of ethanol and stirred for at least 48 hours. After stirring, the solution was dosed on hydrophobized glass having the wettability by demi water of 61° (+/−2°) and dried in a closed space, in a temperature gradient at the temperature of the lower plate 50° C. and the temperature of the upper plate 20° C. for 12 hours. After drying, the film was evaluated, removed from the substrate and characterized. The thickness of the thus prepared film was determined to be about 15 µm.

Example 18. Preparation of the Film Based on Palmitoyl Derivative of Sodium Hyaluronate 100 mg of palmitoyl derivative of sodium hyaluronate having the substitution degree of 31% and molecular weight $2.7 \times 10^5$ g/mol were dissolved in 20 ml of 50% solution of propan-2-ol and stirred for at least 20 hours. After stirring, the solution was dosed on hydrophobized glass having the wettability by demi water of 61° (+/−2°) and dried in a closed space, in a temperature gradient at the temperature of the lower plate 50° C. and the temperature of the upper plate 20° C. for 12 hours. After drying, the film was evaluated, removed from the substrate and characterized. The thickness of the thus prepared film was determined to be about 15 µm.

Example 19. Preparation of the Film Based on Lauroyl Derivative of Sodium Hyaluronate 100 mg of lauroyl derivative of sodium hyaluronate having the substitution degree of 58% and molecular weight $1.88 \times 10^5$ g/mol were dissolved in 20 ml of 50% solution of propan-2-ol and stirred for at least 48 hours. After stirring, the solution was dosed on hydrophobized glass having the wettability by demi water of 61° (+/−2°) and dried in a closed space, in a temperature gradient at the temperature of the lower plate 20° C. and the temperature of the upper plate 10° C. for 12 hours. After drying, the film was evaluated, removed from the substrate and characterized. The thickness of the thus prepared film was determined to be about 15 µm.

Example 20. Comparison of Substrate Wettabilities Obtained by Using Various Hydrophobization Agents The glass intended for hydrophobization was first cleaned thoroughly so that the resulting demi water wettability would not be above 10°. Then the hydrophobization of the glass was conducted. For the hydrophobization of the glass, the following hydrophobization agents were used: chlorotrimethylsilane (CTMS), (3-aminopropyl)trimethoxysilane (APTMS) and octadecyltrichlorosilane (OTS). The resulting values of the glass wettability (with the concentration of the agent being 1%) are listed in Table 1. Moreover, for CTMS, various concentrations of the agent in hexane were tested. The obtained values of the measured glass wettabilities are listed in Table 2.

TABLE 1 glass wettability expressed by the contact angle upon hydrophobization by an agent having the concentration of 1%

| Agent (1%) | Solvent | CA |
| --- | --- | --- |
| CTMS | hexane | approx. 70° |
| APTMS | hexane | approx. 90° |
|  | acetone | approx. 70° |
|  | dichloromethane | approx. 90° |

TABLE 1-continued glass wettability expressed by the contact angle upon hydrophobization by an agent having the concentration of 1%

| Agent (1%) | Solvent | CA |
| --- | --- | --- |
| OTS | ethanol (96%) | approx. 66° |
|  | toluene | approx. 105° |
|  | propan-2-ol | approx. 103° |

CA means contact angle

TABLE 2 glass wettability expressed by the contact angle upon hydrophobization by various concentrations of CTMS in hexane

| Concentration of CTMS | CA |
| --- | --- |
| 0.10% | approx. 50° |
| 0.50% | approx. 60° |
| 1% | approx. 70° |
| 3-5% | <80° |

CA means contact angle

Example 21. Determination of the Hydrophobization Agent Residues in the Film Prepared According to Example 1

Trimethylsilanol was analysed as a residuum of trimethylsilyl chloride after its reaction with the —OH groups of the hyaluronan derivative. The analysis was carried out on a gas chromatograph equipped with a headspace sampler and a mass spectrometry detector in the form of a simple quadrupole. A sample of the film prepared according to Example 1 was dissolved to the concentration of 6 mg/ml in 50% (vol./vol.) propan-2-ol and upon dissolution, 4.75 ml of the sample and 0.25 ml of n-butanol (1 mg/ml), which acted as an internal standard, were pipetted into a vial. A stock solution of trimethylsilyl chloride (1 mg/ml) was prepared in 50% propan-2-ol as well, which reacted to trimethylsilanol immediately. From this solution, a calibration series ranging from 0.5 to 15.0 µg/ml was prepared, with the addition of n-butanol as an internal standard. No analysed film sample proved the presence of trimethylsilanol in a concentration higher than the first calibration point, i.e., the content of trimethylsilanol in the film samples was lower than 0.008 wt. %.

Example 22. Effect of the Adhesion of the Film Based on an Oleyl Derivative of Sodium Hyaluronate on the Surface Appearance Thereof The films prepared according to Examples 10 and 11 were prepared on two glasses having different wettabilities, namely 57° (+/−3°) and 107° (+/−1°). After drying, the surface appearance of the film was evaluated and correlated with the adhesion. In the case of a good adhesion of the film to the substrate, the film surface is flat, without any surface deformations. The film was completely adhered to the substrate having a lower contact angle, on the substrate having a higher contact angle it was partially peeled off and deformed. The results are documented on FIGS. 1a, 1b, 1c. The figures imply that if the film is fully adhered to the surface, it is even and without surface deformations after being peeled off (FIG. 1c right). Conversely, in the case of an imperfect adhesion the film is more or less deformed (FIG. 1c left).

Figure 2:
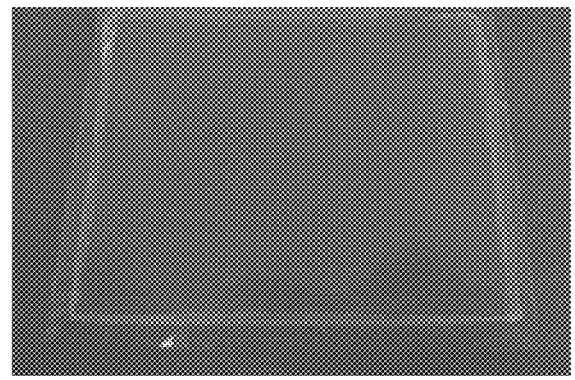
FIG. 2: effect of the adhesion of the film on the basis of the palmitoyl derivative of sodium hyaluronate on the surface appearance thereof

Example 23. Effect of the Adhesion of the Film Based on a Palmitoyl Derivative of Sodium Hyaluronate on the Surface Appearance Thereof The film based on the palmitoyl derivative of sodium hyaluronate prepared according to Example 2 on a glass having the wettability of 61° (+/−2°) was evaluated. After drying, the adhesion and the appearance of the film were evaluated. The film was well adhered and its surface was absolutely flat, without any deformations. The result of the adhesion is documented in FIG. 2.

Example 24. Determination of the Residual Propan-2-ol in the Films

The residual concentration of the organic solvent propan-2-ol was determined by means of gas chromatography in the films prepared according to Examples 1, 8 and 12. The principle of the determination of the solvent is the conversion thereof into the gaseous phase at an elevated temperature, the separation thereof on the gas chromatograph and the subsequent detection by the flame ionization detector. The concentration of propan-2-ol in the film was always determined twice (i.e., for two samples), by reading from the calibration curve. The sample weight was always 50 mg. After completing the analysis, the concentration of the residual propan-2-ol was determined in all films to be lower than the lowest calibration curve point and was expressed as <0.02 wt. %. This value safely fulfils the requirements on the amounts of residual solvents of class 3 according to the EU pharmacopoeia.

Example 25. Determination of the Weight—Homogeneity within the Area

The film prepared according to Example 1 was cut into 55 squares with an area of 1 cm². Prior to the measurement, the individual samples were left at room humidity and temperature for 5 hours. Then the individual squares were weighed on analytical scales. The obtained weights of the individual squares are listed in Table 3. The average, standard deviation and variation coefficient were calculated based on all the values listed in the Table. The calculated values: average 2.35 mg, standard deviation 0.18 mg, variation coefficient 7.51%.

TABLE 3 determination of the weight homogeneity of the film

| 2.6 | 2.3 | 2.4 | 2.6 | 2.4 | 2.2 | 2.1 | 2.6 | 2.1 | 2.1 | 2.5 |
| --- | --- | --- | --- | --- | --- | --- | --- | --- | --- | --- |
| 2.5 | 2.3 | 2.7 | 2.6 | 2.5 | 2.6 | 2.0 | 2.6 | 2.1 | 2.5 | 2.4 |
| 2.5 | 2.2 | 2.3 | 2.4 | 2.3 | 2.2 | 2.3 | 2.6 | 2.2 | 2.2 | 2.3 |
| 2.3 | 2.4 | 2.2 | 2.2 | 2.5 | 2.7 | 2.5 | 2.3 | 2.3 | 2.5 | 2.3 |
| 2.1 | 2.1 | 2.1 | 2.3 | 2.3 | 2.3 | 2.4 | 2.2 | 2.2 | 2.3 | 2.4 |

Example 26. Determination of the Thickness—Homogeneity within the Area

A square grid having the area of one square 1 cm² and the total number of squares 35 was drawn on the film prepared according to Example 15. On each square, the thickness of the film was measured by means of a mechanical thickness meter Mytutoyo VL-50. The measurement was conducted in a stable environment having the humidity of 50% and the temperature of 25° C. The measured values are listed in Table 4. The average, standard deviation and variation coefficient were calculated based on all values listed in the Table. The calculated values: average 14.6 μm, standard deviation 1.17 μm, variation coefficient 8.02%.

TABLE 4 determination of the thickness homogeneity, the listed values are in μm

| 16.2 | 16.7 | 16.2 | 15.2 | 13.8 | 13.8 | 14.7 |
|------|------|------|------|------|------|------|
| 13.9 | 13.9 | 13.9 | 13.7 | 13.4 | 13.2 | 14.3 |
| 14.8 | 13.9 | 14.1 | 13.3 | 12.8 | 13.5 | 14.6 |
| 16.9 | 16.2 | 16.6 | 15.7 | 15.6 | 15.0 | 16.2 |
| 14.7 | 14.9 | 15.0 | 14.7 | 13.7 | 12.5 | 13.8 |

Example 27. Comparison of the Swelling Capacities of the Films Prepared from Palmitoyl Derivatives of Sodium Hyaluronate Having Various Substitution Degrees in 0.1M Phosphate Buffer, pH 7.4

Films prepared according to Examples 2, 16 and 17 were cut to precisely defined squares, weighed, measured and inserted into 0.1M phosphate buffer (PBS), pH 7.4. At 37° C., the swelling capacity of the films was monitored; each experiment was done in triplicate. The changes in the weight and dimensions of the film were evaluated—the results are listed in Table 5. It is evident from this Table that the lower is the substitution degree, the higher is the swelling capacity of the film. In case of using high substitution degrees, only a small change of the film area can be achieved, which may be very important in a number of applications.

TABLE 5 swelling capacity of the films prepared from palmitoyl derivatives having various substitution degrees

|  | area change after 5 days in 0.1M PBS, pH 7.4 (%) | weight change after 5 days in 0.1M PBS, pH 7.4 (%) |
|---|---|---|
| Film prepared according to Example 16 | 69 | 1365 |
| Film prepared according to Example 17 | 32 | 749 |
| Film prepared according to Example 2 | 15 | 496 |

Figure 3:
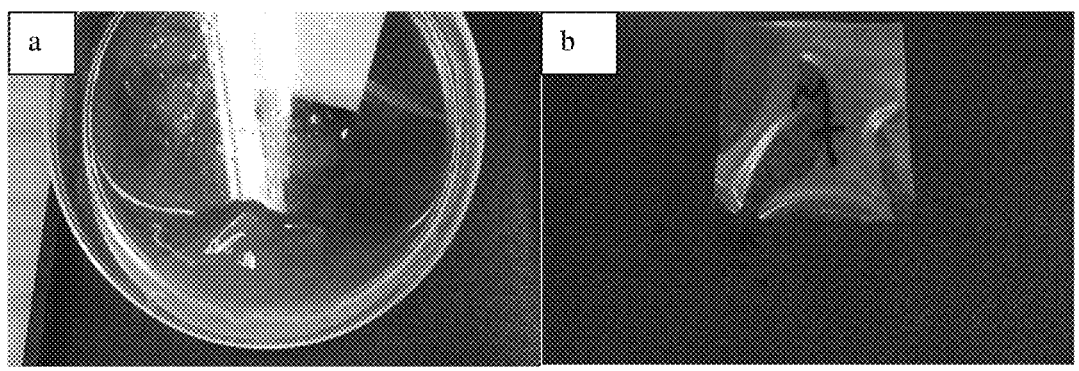
FIG. 3: comparison of the films prepared according to Examples 2 (b) and 18 (a) after 3 weeks of degradation in a conditioned medium

Example 28. Degradation of the Films Prepared from Palmitoyl Derivative of Sodium Hyaluronate in a Conditioned Medium—Comparison of Two Substitution Degrees Films prepared according to Examples 2 and 18 were cut to precisely defined squares, weighed, measured and inserted into a conditioned medium. All preparation proceeded in a laminar box so that no contamination and undesirable reactions of the medium occur. At 37° C., the change of the area of the film and the visual appearance thereof were checked in predetermined intervals, which properties may be associated with the degradation. The conditioned medium was exchanged in regular intervals; the experiment was conducted in triplicate. The film prepared according to Example 2 began to degrade significantly later than the film prepared according to Example 18. The results are shown in FIGS. 3a and 3b, where the appearance of the film is shown after 3 weeks of degradation in the conditioned medium. Table 6 documents the change of the film area after 1 week of degradation for the film according to Example 2, as well as to Example 18, and after three weeks for the film according to Example 2 (the film according to Example 18 was degraded to pieces or even dissolved after three weeks of degradation). Based on the results it is obvious that the degradation rate depends significantly on the substitution degree of sodium hyaluronate by the acyl chain. In the case of a highly substituted film prepared according to Example 2, the degradation proceeded in terms of several months.

TABLE 6 change of the film area after 1 week in a conditioned medium - comparison of two substitution degrees

|  | change of the area of the film after 1 week in the conditioned medium (%) |
|---|---|
| Film prepared according to Example 2 | 13 |
| Film prepared according to Example 18 | 125 |

Figure 4:
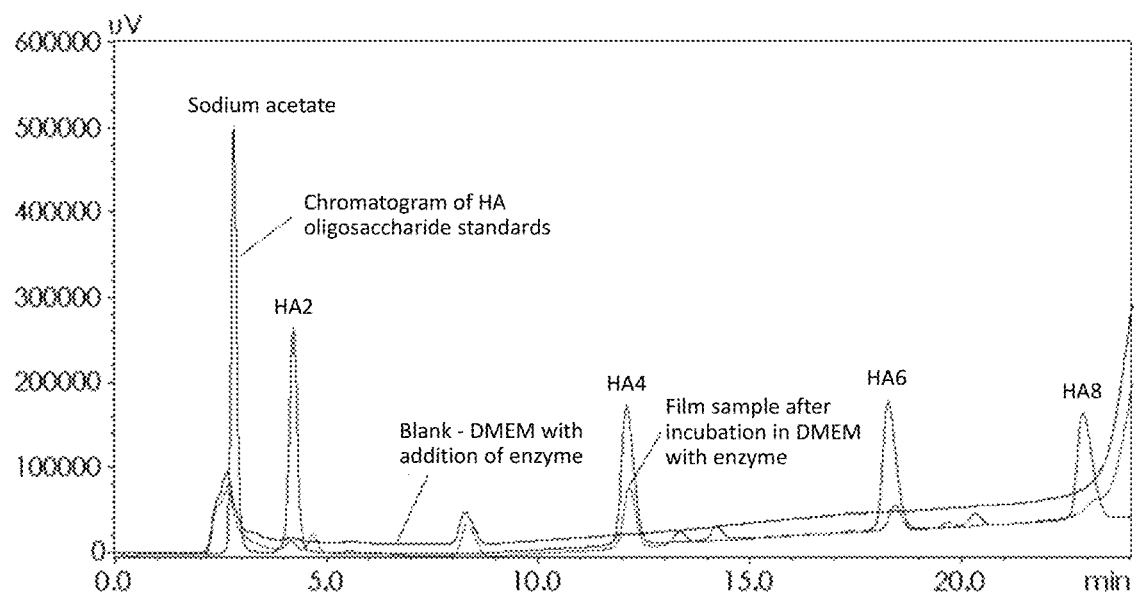
FIG. 4: Proof of the presence of HA-based oligosaccharides in the solution of the film according to Example 5 (DS=20%) after incubation in DMEM (Dulbecco's modified Eagle's medium) with an addition of an enzyme, by means of HPLC. The figure shows 3 chromatograms corresponding to (i) separation of HA oligosaccharide standards (standard HA2 ($t_R$=4.1 min), HA4 ($t_R$=12 min), HA6 ($t_R$=18.1 min), HA8 ($t_R$=22.9 min)), (ii) a blank sample—DMEM with an addition of an enzyme and (iii) solution in which the incubation of the film was carried out.

Example 29. Degradation of the Film Based on a Palmitoyl Derivative of Sodium Hyaluronate Samples of the film prepared according to Example 5 were incubated in a standard medium for cell cultures (Dulbecco's modified Eagle's medium) with the addition of 300 IU of an enzyme per 1 mg of the film. The incubation proceeded at 37° C. and the samples were analysed after 24 hours. The sample analysis was conducted on the HPLC system Alliance (Waters) according to an internal standard operating procedure. After 24 hours, it was still possible to observe non-degraded pieces of the film. In spite of that, oligosaccharides based on hyaluronan were detected in the solution, as shown in FIG. 4.

Example 30. Degradation of the Film Based on a Palmitoyl Derivative of Sodium Hyaluronate Samples of the film prepared according to Example 2 were incubated in a standard medium for cell cultures (Dulbecco's modified Eagle's medium) with the addition of 300 IU of an enzyme per 1 mg of the film. The incubation proceeded at 37° C. and the samples were analysed after 24 hours. The sample analysis was conducted on the HPLC system Alliance (Waters) according to an internal standard operating procedure. After 24 hours, no oligosaccharides based on hyaluronan were detected in the solution, which is in accordance with Example 28, where a very long degradation time was observed for the film according to Example 2, and which demonstrates the possibility of degradation modulation by means of the substitution degree.

Example 31. Characterization of the Films by Means of Young's Modulus

Young's modulus was determined for films prepared according to Examples 10, 15, 16 and 19 in the dry state. The films were tested for mechanical properties by means of a single stage tensile testing machine INSTRON3343 with a 100N head. The Young's modulus was calculated based on the mean value of at least 9 valid measurements. Table 7 shows that the Young's modulus of dry, non-hydrated films does not depend on the molecular weight, substituent or substitution degree.

TABLE 7

Young's modulus of the films

| | Young's modulus (MPa) |
|---|---|
| Film prepared according to Example 10 | 2835 (+/− approx. 10%) |
| Film prepared according to Example 15 | 2409 (+/− approx. 10%) |
| Film prepared according to Example 16 | 1800 (+/− approx. 10%) |
| Film prepared according to Example 19 | 2636 (+/− approx. 10%) |

Figure 5:
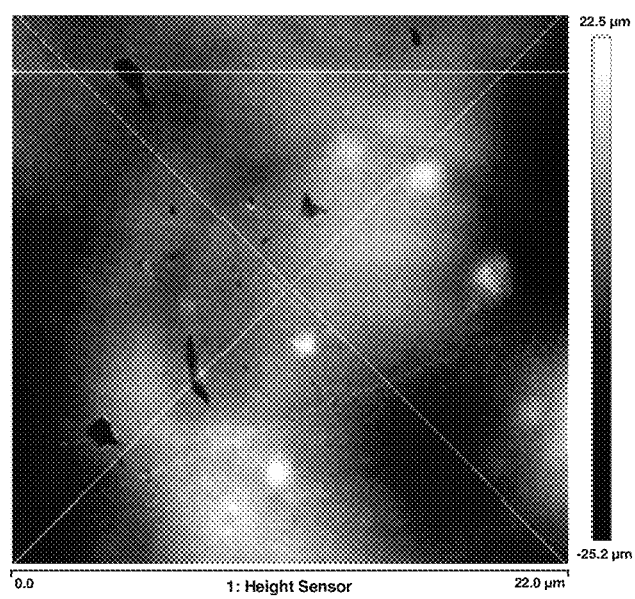
FIG. 5: morphology of the film prepared according to Example 16 from the substrate side

Example 32. Characterization of the Film Surface Morphology and Determination of RMS by Means of AFM The films prepared according to Examples 8 and 16 were characterized by means of the Atomic force microscopy (AFM) method, wherein especially the appearance and the character of the surface were monitored. Especially the RMS roughness (root mean square roughness) was determined. It was found out that a very smooth surface having the RMS value up to 2 um may be obtained from the side of the substrate (see FIG. 5 for the film according to Example 16). The side of the film that is exposed to the air during drying is always rougher, wherein RMS is somewhere around 50 or more nm.

Example 33. Comparison of Films Dried in a Temperature Gradient and in a Closed Space The films prepared according to Examples 8 and 19 were visually compared after drying. The surface of both films was not deformed, the surface crust did not form on any of the films. Both films were qualitatively the same (visual comparison).

Figure 6:
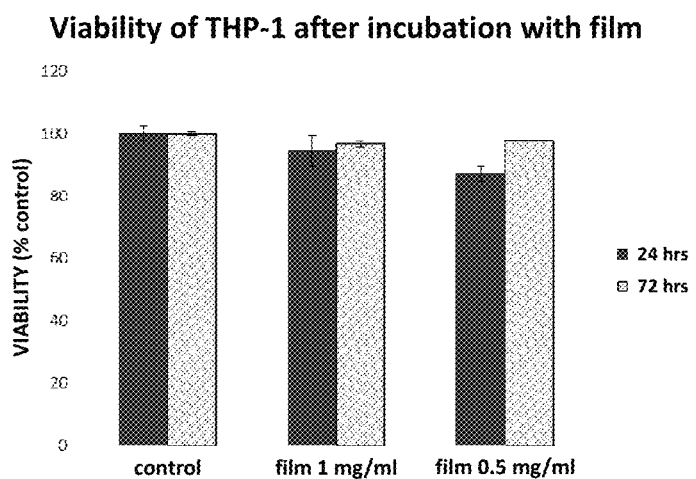
FIG. 6: viability of the suspension THP-1 cells after 24 and 72 hours of incubation with the film prepared according to Example 1 based on the palmitoyl derivative of sodium hyaluronate

Example 34. Viability of THP-1 Suspension Cells after 24- and 72-Hour Incubation with the Film Prepared According to Example 1 Based on a Palmitoyl Derivative of Sodium Hyaluronate The THP-1 cell line was cultured in a medium with the addition of 10% fetal bovine serum. After achieving a sufficient density and viability (measured by means of an automatic cell calculator CASY TT, Roche), the cells were seeded into a 6-well panel in 2 ml of 10% medium. The tested film was added to the cells in an amount of 1 and 0.5 mg/ml. After 24 and 72 hours of incubation, the cells were washed and their viability and the occurrence of cell death were detected by means of the detection kit ApoFlowEx® FITC Kit (Exbio) on a flow cytometer MACSQuant® (Miltenyi Biotec). The cells were evaluated as viable in case no propidium iodide fluorescence was detected. FIG. 6 shows a negligible reduction of the viability after 24 hours of incubation, which was not detected anymore after 72 hours. Therefore, the tested film is evaluated as non-cytotoxic in said concentrations.

Example 35. Analysis of the Cell Death of THP-1 Suspension Cells after 24 and 72 Hours of Incubation with the Film Prepared According to Example 1 on the Basis of Palmitoyl Derivative of Sodium Hyaluronate The THP-1 cell line was cultured in a medium with the addition of 10% fetal bovine serum. After achieving a sufficient density and viability (measured by means of an automatic cell calculator CASY TT, Roche), the cells were seeded into a six-well panel in 2 ml of 10% medium. The tested film was added to the cells in an amount of 1 and 0.5 mg/ml. After 24 and 72 hours of incubation, the cells were washed and their viability and the occurrence of cell death were detected by means of the detection kit ApoFlowEx® FITC Kit (Exbio) on the flow cytometer MACSQuant® (Miltenyi Biotec). The evaluation of the presence of cell death (apoptosis and necrosis) was conducted according to the recommendation of the kit producer. In brief: the population of the individual cells was divided based on the fluorescence intensity of propidium iodide and Annexin V-FITC into 3 groups: negative in both channels (living cells), positive just in the channel for Annexin V-FITC (apoptotic cells) and positive cells for the channel propidium iodide+/−Annexin V-FITC (necrotic cells).

Figure 7:
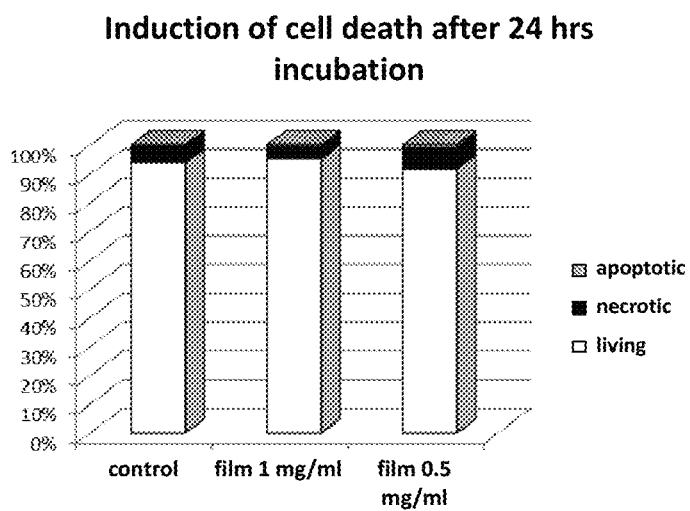
FIG. 7: induction of the cell death after 24 hours of incubation with the film prepared according to Example 1 based on the palmitoyl derivative of sodium hyaluronate
Figure 8:
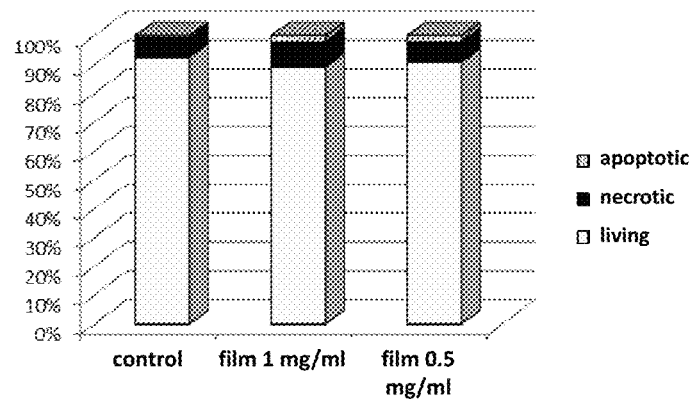
FIG. 8: induction of the cell death after 72 hours of incubation with the film prepared according to Example 1 based on the palmitoyl derivative of sodium hyaluronate

FIGS. 7 and 8 imply that after 24, as well as 72 hours, no greater increase of the number of apoptotic or necrotic cells in the culture occurs and the tested material may therefore be evaluated as not inducing cell death.

Example 36. Contact Inhibition of the Growth of Mouse 3T3 Swiss Fibroblasts

The mouse 3T3 Swiss fibroblast line was cultured in a medium with the addition of 10% fetal bovine serum. In the exponential growth phase, the cells were seeded into a six-well panel in 2 ml of the 10% medium. After achieving confluency, the tested film prepared according to Example 1 having the area of 1 cm$^2$ was added, which was loaded by a silicon sterile ring so that no significant movement of the film on the monoculture occurs. At the same time, control cells were incubated without any treatment and just with the silicon ring. After 72 hours of incubation, the film samples and the silicon rings were removed, the cells were washed with PBS and fixed by 4% formaldehyde (10 min/room temperature). After washing with deionized water, the cells were coloured with crystal violet (0.1% in water, 30 min/room temperature) and after washing the colour away the cell area was photographed and observed under a light microscope. The cell area under the tested material, the extent of the damage of the cells and the size of the damaged zone were evaluated.

Figure 9:
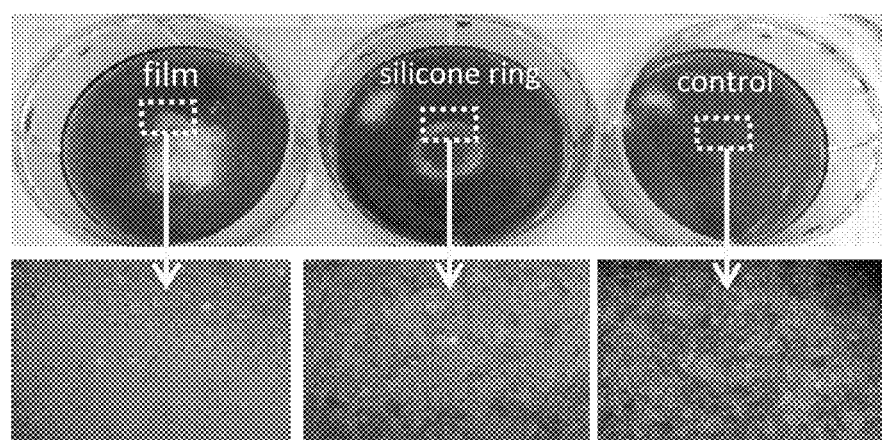
FIG. 9: contact inhibition of the growth of mouse 3T3 Swiss fibroblasts caused by the film prepared according to Example 1.

Macrophotographs (FIG. 9) clearly show that the damaged zone of the monolayer is delimited and that only the cells which were directly under the film were damaged, most probably by a slight friction; the details from the light microscope show that the cells tended to re-grow under the film. Neither any damage nor a change in morphology of the cells at the borders of the tested film were observed. Therefore, it can be assumed that the material does not exhibit the contact inhibition of the cell growth.

Example 37. Cell Antiadhesive Properties of the Film

Figure 10:
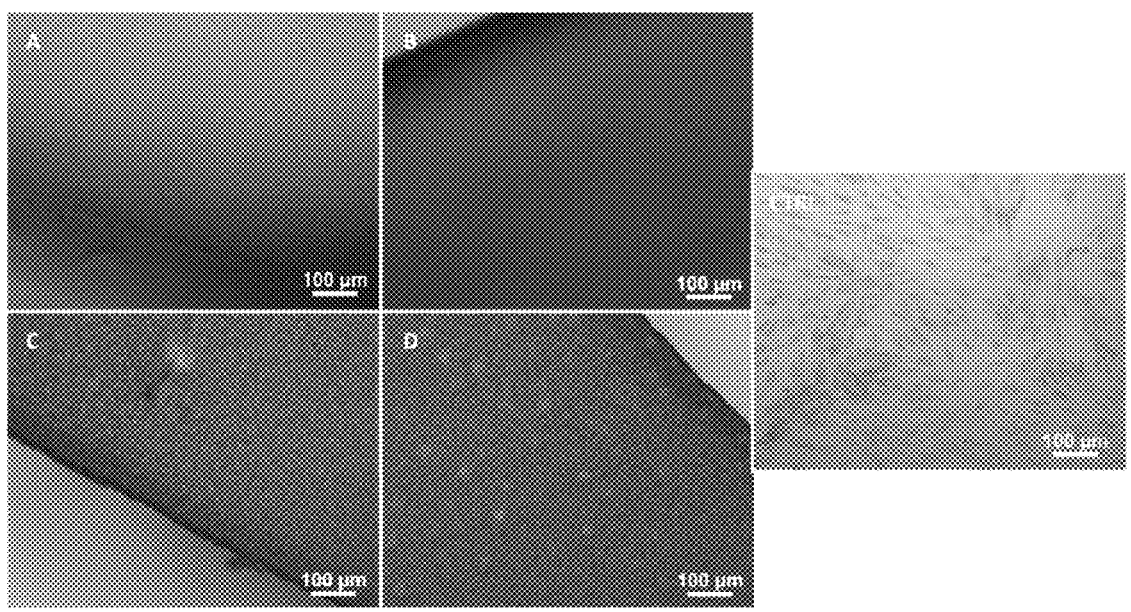
FIG. 10: cell antiadhesive properties of the film, A—the film prepared according to Example 17, upper surface of the film, B—the film prepared according to Example 17, lower surface of the film, C—the film prepared according to Example 2, upper surface of the film, D—the film prepared according to Example 2, lower surface of the film, CTRL—control

The films prepared according to Examples 2 and 17 (derivatives having two different substitution degrees) were cut in a sterile manner to parts having the dimensions of 1 cm$^2$. These parts were placed into a six-well culture panel face-up or face-down. Then they were loaded with sterile silicon rings and culture medium (2 ml) for primary human fibroblasts (NHDF) containing 10% fetal bovine serum was pipetted to the thus prepared samples. Meanwhile, a NHDF suspension was prepared and pipetted to the middle of the silicon ring on the film surface in an amount of 100 000 cells/sample. The samples with the cells were incubated for 72 hours and checked in 24-hour intervals under the light microscope. Polystyrene adapted for cell cultures with good adhesion properties was used as a positive control (CTRL). After completion of the incubation, the silicon rings were removed and the films together with the cells were fixed by 4% formaldehyde for 10 minutes and then coloured with 1% crystal violet in water (10 min). After washing the unbound crystal violet away thoroughly (2×5 min rinse with distilled water), the samples were photographed using an inverted microscope Nikon with 100× magnification. The results are shown in FIG. 10. On the CTRL photo, an almost confluent cell layer may be seen. On the film photos (A-D), a certain structure is observable, probably formed due to the long incubation in the medium and made visible by means of crystal violet. However, no cells are present on the films. It can therefore be stated that the films are completely non-adherent in this system and even the presence of proteins in the culture medium did not promote the adhesion.

Example 38. Preparation of the Film with Octenidine Dihydrochloride

20 μl of a stock solution of octenidine dihydrochloride in ethanol having the weight concentration of 10 mg/ml were mixed with 20 ml of 50% propan-2-ol. After stirring thoroughly, 100 mg of a palmitoyl derivative of sodium hyaluronate having the substitution degree of 57% and molecular weight of $2.67 \times 10^5$ g/mol were added to the solution. The solution was stirred for 72 hours and after stirring it was dosed on a hydrophobized glass having the wettability value of 65 (+/−3°) and dried in a closed space, in a temperature gradient at the temperature of the lower plate 50° C. and the temperature of the upper plate 20° C. for 6 hours. After drying, the film was evaluated, removed from the substrate and characterized. The thickness of the film was determined to be 15 μm.

The invention claimed is:

1. A film based on a hyaluronic acid ester, characterized by that it comprises a $C_{10}$-$C_{22}$-acylated derivative of hyaluronic acid according to the general formula (I)

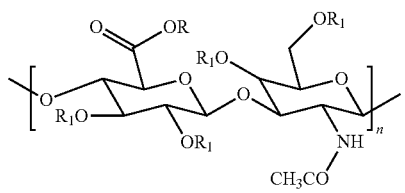

where R is $H^+$ or $Na^+$, and where $R^1$ is H or $C(=O)C_xH_y$, where x is an integer within the range from 9 to 21 and y is an integer within the range from 11 to 43 and $C_xH_y$ is a linear or branched, saturated or unsaturated chain $C_9$-$C_{21}$, wherein in at least one repeating unit one or more of $R^1$ is $—C(=O)C_xH_y$ and where n is within the range from 12 to 4000; and wherein the film is self-supporting, the thickness of the film is homogeneous and is within a range of 2 μm to 100 μm, and the Young's modulus of the film is within a range from 1 to 5000 MPa in the dry state, and the surface roughness expressed in the form of a root mean square of at least one of the film surfaces is within the range from 0.5 to 100 nm.

2. The film according to claim 1, characterized by that it comprises palmitoyl hyaluronan or lauroyl hyaluronan.

3. The film according to claim 1 or claim 2, characterized by that the $C_{10}$-$C_{22}$-acylated derivative of hyaluronic acid has the molecular weight from $1 \times 10^5$ to $1 \times 10^6$ g/mol.

4. The film according to claim 1 or claim 2, characterized by that the $C_{10}$-$C_{22}$-acylated derivative of hyaluronic acid has the substitution degree within the range from 15 to 160% relative to hyaluronan dimers.

5. The film according to claim 1 or claim 2, characterized by that it has the thickness within the range from 5 to 25 μm.

6. The film according to claim 1 or claim 2, characterized by that it further comprises at least one biologically active substance selected from the group including pharmaceutically active substances and cosmetically active substances.

7. The film according to claim 1 or claim 2 for use in medical applications or biotechnological applications.

8. The film according to claim 7 for use in the construction of a medical device.

9. A method of preparation of the film defined in claim 1 or claim 2, characterized by that a solution comprising a $C_{10}$-$C_{22}$ acylated derivative of hyaluronic acid according to the general formula (I) is prepared in a mixture of water and $C_1$-$C_6$ alcohol, which is stirred, and then applied on a substrate and dried in a closed space, and then is removed from the substrate.

10. The method of preparation of the film according to claim 9, characterized by that the ratio of the mixture of $C_1$-$C_6$ alcohol and water is within the range from 25-55 vol. % to 45-75 vol. %, wherein the amount of the $C_{10}$-$C_{22}$ acylated derivative of hyaluronic acid in the solution is within the range from 0.5 to 3 wt. %.

11. The method of preparation of the film according to claim 9, characterized by that the solution is stirred for 20 to 72 hours.

12. The method of preparation of the film according to claim 9, characterized by that the drying takes place at a temperature within the range from 20° C. to 50° C. for 3 to 6 hours.

13. The method of preparation of the film according to claim 9, characterized by that the drying takes place in a temperature gradient, where the lower film surface lying on the substrate is heated to a temperature that is at least 1° C. higher than the temperature to which the opposite upper surface of the film is heated or cooled.

14. The method of preparation of the film according to claim 13, characterized by that the lower surface of the film lying on the substrate is heated to the temperature within the range from 20° C. to 60° C. and the opposite upper surface of the film is heated or cooled to the temperature within the range from 10° C. to 59° C.

15. The method of preparation of the film according to claim 13 or claim 14, characterized by that the film is dried in a temperature gradient for 6 to 12 hours.

16. The method of preparation of the film according to claim 9, characterized by that at least one biologically active substance is admixed to the solution, the substance being selected from the group consisting of pharmaceutically and cosmetically active substances, vitamins, drugs, cytostatics, steroids, phytoextracts, phytocomplexes, and phytoactive substances.

17. The method of preparation of the film according to claim 9, characterized by that the substrate is a polymer selected from the group consisting of polyvinyl alcohol, polypropylene, polyethylene, polyoxymethylene, polystyrene, and hydrophobized glass, wherein the contact wetting angle of the substrate surface by demi water is within the range from 30° to 120°.

\* \* \* \* \*

UNITED STATES PATENT AND TRADEMARK OFFICE
CERTIFICATE OF CORRECTION

PATENT NO. : 10,689,464 B2
APPLICATION NO. : 15/556370
DATED : June 23, 2020
INVENTOR(S) : Marcela Dusankova et al.

It is certified that error appears in the above-identified patent and that said Letters Patent is hereby corrected as shown below:

On the Title Page

Page 3, item (56) Column 2, Line 19, "Modem" should be --Modern--.

Page 9, item (56) Column 1, Line 67, "propeties,"" should be --properties,"--.

Page 9, item (56) Column 2, Line 67, "recentadvances" should be --recent advances--.

In the Specification

Column 3, Line 7, "dimetylsulfoxide" should be --dimethylsulfoxide--.

Column 5, Line 37, "masons," should be --reasons,--.

Column 19, Line 22, "urn" should be --nm--.

In the Claims

Column 21, Line 54, Claim 1 (after formula), "$C(=O)C_xH_y$," should be -- $–C(=O)C_xH_y$,--.

Signed and Sealed this
Twentieth Day of October, 2020

Andrei Iancu
*Director of the United States Patent and Trademark Office*